United States Patent
Kobayashi et al.

(10) Patent No.: US 11,191,524 B2
(45) Date of Patent: Dec. 7, 2021

(54) ULTRASONIC DIAGNOSTIC APPARATUS AND NON-TRANSITORY COMPUTER READABLE MEDIUM

(71) Applicant: Canon Medical Systems Corporation, Otawara (JP)

(72) Inventors: Yukifumi Kobayashi, Yokohama (JP); Koichiro Kurita, Nasushiobara (JP); Yutaka Kobayashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 452 days.

(21) Appl. No.: 16/145,574

(22) Filed: Sep. 28, 2018

(65) Prior Publication Data

US 2019/0090855 A1    Mar. 28, 2019

(30) Foreign Application Priority Data

Sep. 28, 2017 (JP) .............................. JP2017-189150
Sep. 26, 2018 (JP) .............................. JP2018-179989

(51) Int. Cl.
*A61B 8/06* (2006.01)
*A61B 8/08* (2006.01)
*A61B 8/14* (2006.01)
*A61B 8/00* (2006.01)
(Continued)

(52) U.S. Cl.
CPC .............. *A61B 8/5246* (2013.01); *A61B 8/06* (2013.01); *A61B 8/14* (2013.01); *A61B 8/4254* (2013.01); *A61B 8/463* (2013.01); *A61B 8/466* (2013.01); *A61B 8/523* (2013.01); *A61B 8/5261* (2013.01); *A61B 5/055* (2013.01); *A61B 6/032* (2013.01); *A61B 6/037* (2013.01); *A61B 8/469* (2013.01); *A61B 8/485* (2013.01); *A61B 8/486* (2013.01);
(Continued)

(58) Field of Classification Search
CPC ....... A61B 8/5055; A61B 6/032; A61B 6/037; A61B 8/06; A61B 8/14; A61B 8/4254; A61B 8/463; A61B 8/466; A61B 8/469; A61B 8/485; A61B 8/486; A61B 8/488; A61B 8/523; A61B 8/5246; A61B 8/5261; A61B 8/5284; A61B 8/543
See application file for complete search history.

(56) References Cited

U.S. PATENT DOCUMENTS

2011/0046485 A1* 2/2011 Nakata ................... A61B 8/486
                                                       600/440
2016/0270757 A1* 9/2016 Toma ..................... A61B 8/463

FOREIGN PATENT DOCUMENTS

JP           10-151131         6/1998

* cited by examiner

*Primary Examiner* — Mark D Remaly
(74) *Attorney, Agent, or Firm* — Oblon, McClelland, Maier & Neustadt, L.L.P.

(57) ABSTRACT

According to one embodiment, an ultrasonic diagnostic apparatus includes processing circuitry. The processing circuitry acquires first echo data in a first mode, and acquires second echo data in a second mode. The processing circuitry sequentially generates a first image including a B-mode image based on the first echo data in the first mode, and sequentially generates a second image not including a B-mode image based on the second echo data in the second mode. The processing circuitry sequentially generates a third image from pre-acquired volume data. The processing circuitry directs a display to sequentially display the first image and the third image in the first mode, and to sequentially display the second image and the third image in the second mode.

17 Claims, 14 Drawing Sheets

(51) Int. Cl.
  *A61B 6/03* (2006.01)
  *A61B 5/055* (2006.01)
(52) U.S. Cl.
  CPC .............. *A61B 8/488* (2013.01); *A61B 8/5284* (2013.01); *A61B 8/543* (2013.01)

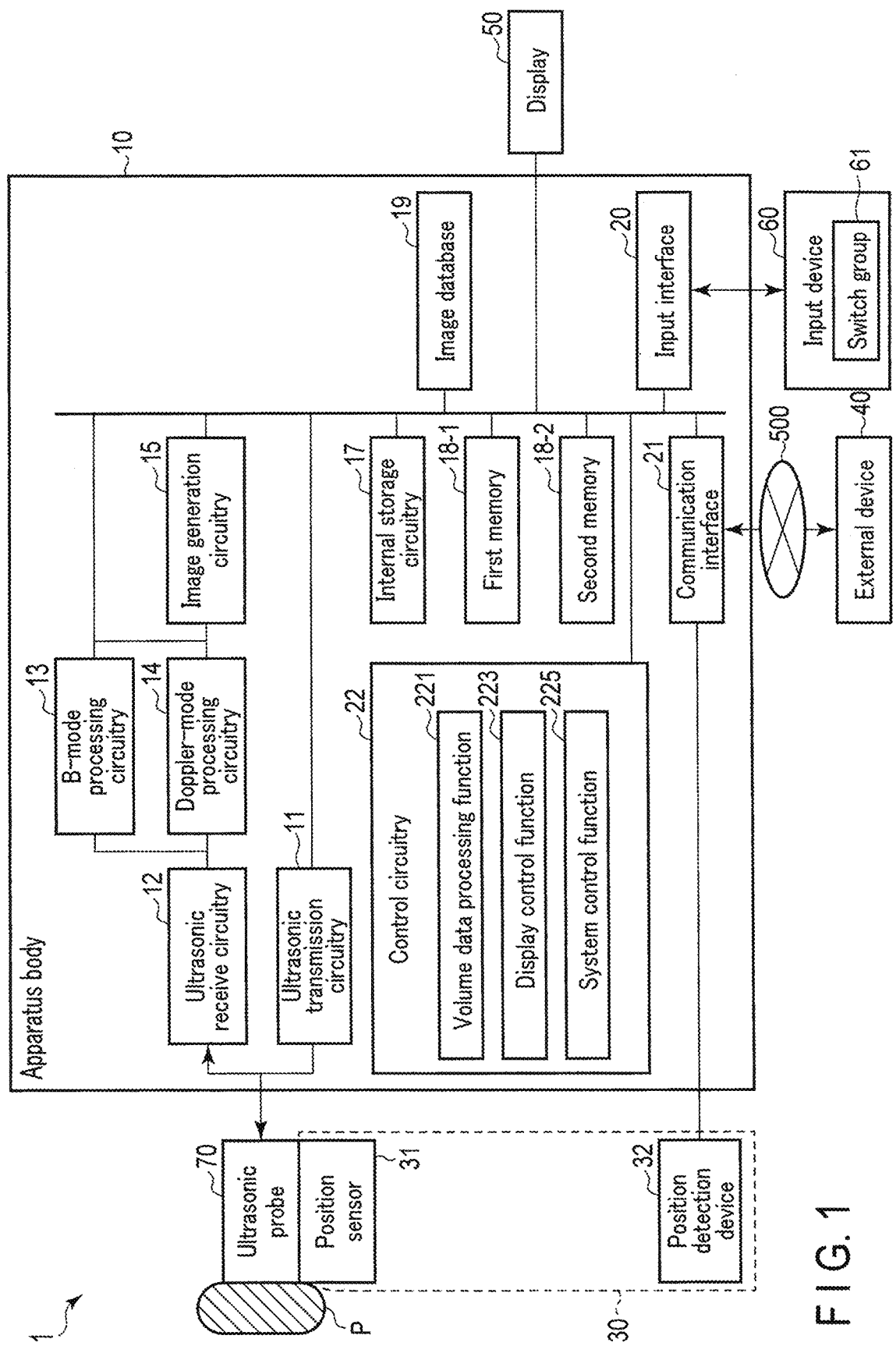
F I G. 1

ULTRASONIC DIAGNOSTIC APPARATUS AND NON-TRANSITORY COMPUTER READABLE MEDIUM

CROSS-REFERENCE TO RELATED APPLICATIONS

This application is based upon and claims the benefit of priority from Japanese Patent Applications No. 2017-189150, filed Sep. 28, 2017; and No. 2018-179989, filed Sep. 26, 2018; the entire contents of both of which are incorporated herein by reference.

FIELD

Embodiments described herein relate generally to an ultrasonic diagnostic apparatus and a non-transitory computer readable medium.

BACKGROUND

Ultrasonic diagnostic apparatuses generally acquire B-mode images in which the echo intensity from the imaging target is expressed by brightness. Usually, the ultrasonic diagnostic apparatuses acquire B-mode images under the condition where an imaging mode (B-mode) to acquire B-mode images is selected.

The ultrasonic diagnostic apparatuses possess imaging modes for acquiring images other than B-mode images, such as Doppler images representing movement of blood or tissues, or tissue property images representing tissue properties. There are cases where the ultrasonic diagnostic apparatuses acquire B-mode images as reference images to recognize an acquisition position of echo data within a subject's body even if an imaging mode other than the B-mode is executed. However, in the case where an object which moves at a high speed is imaged, or where it requires a long time to acquire a frame image, B-mode images may not be acquired to ensure the quality of images other than B-mode images. By not acquiring B-mode images, the updating of B-mode images is performed less often, and an operator may have difficulty in recognizing the acquisition position of echo data.

BRIEF DESCRIPTION OF THE DRAWINGS

FIG. 1 illustrates an example configuration of an ultrasonic diagnostic apparatus according to the first embodiment.

DETAILED DESCRIPTION

Figure 2:
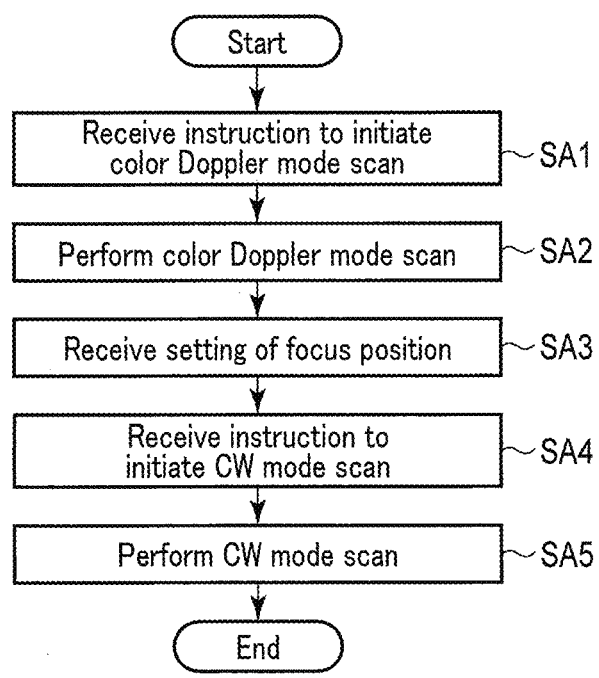
FIG. 2 is a flowchart illustrating the operation in control circuitry shown in FIG. 1 when generating Doppler spectrum image data.

In general, according to one embodiment, an ultrasonic diagnostic apparatus includes processing circuitry. The processing circuitry receives a switching instruction to switch imaging modes from a first imaging mode to a second imaging mode. The processing circuitry acquires first echo data by an ultrasonic probe executing an ultrasonic scan of a first scanning type in the first imaging mode, and acquires second echo data by the ultrasonic probe executing an ultrasonic scan of a second scanning type in the second imaging mode. The processing circuitry sequentially generates a first image including a B-mode image based on the first echo data in the first imaging mode, and sequentially generates a second image not including a B-mode image based on the second echo data in the second imaging mode. The processing circuitry sequentially generates a third image from pre-acquired volume data, based on positional information acquired by a position sensor provided in the ultrasonic probe. The processing circuitry directs a display to sequentially display the first image and the third image in the first imaging mode, and to sequentially display the second image and the third image in the second imaging mode.

Hereinafter, the embodiments of the ultrasonic diagnostic apparatus and the control program will be explained in detail with reference to the accompanying drawings.

First Embodiment

As shown in FIG. 1, an ultrasonic diagnostic apparatus 1 includes an apparatus body 10, an ultrasonic probe 70, a display 50, and an input device 60. The apparatus body 10 is connected to an external device 40 via a network 500. The apparatus body 10 is also connected to a position sensor system 30, the display 50, and the input device 60.

The position sensor system 30 is a system for acquiring three-dimensional positional information of the ultrasonic probe 70 and an ultrasonic image. The position sensor system 30 includes a position sensor 31 and a position detection device 32.

The position sensor system 30 acquires three-dimensional positional information of the ultrasonic probe 70 by using a magnetic sensor, an infrared sensor, or a target for an infrared camera, etc. attached to the ultrasonic probe 70 as the position sensor 31. The position sensor system 30 may acquire the three-dimensional positional information of the ultrasonic probe 70 by a gyro sensor (angular velocity sensor) installed in the ultrasonic probe 70. The position sensor system 30 may acquire the three-dimensional positional information of the ultrasonic probe 70 by imaging the ultrasonic probe 70 by a camera and performing image recognition processing to the image of the ultrasonic probe

70. The position sensor system 30 may detect a three-dimensional position of a robot arm that holds the ultrasonic probe 70 and may acquire the position of the robot arm as the three-dimensional positional information of the ultrasonic probe 70.

Hereinafter, the case where the position sensor system 30 acquires positional information of the ultrasonic probe 70 using the magnetic sensor will be explained as an example. Specifically, the position sensor system 30 further includes a magnetic generator (not shown) having, for example, a magnetic generating coil. The magnetic generator forms a magnetic field oriented outward from the magnetic generator itself. A magnetic space in which location accuracy is assured is defined in the formed magnetic field. The magnetic generator may be arranged so that a living body to be examined is placed within the magnetic space in which location accuracy is assured. The position sensor 31 attached to the ultrasonic probe 70 detects the strength and the gradient of a three-dimensional magnetic field formed by the magnetic generator. By this detection, the position sensor 31 can acquire a position and an orientation of the ultrasonic probe 70. The position sensor 31 outputs the detected strength and gradient of the magnetic field to the position detection device 32.

The position detection device 32 calculates, for example, a position of the ultrasonic probe 70 in the three-dimensional space in which a predetermined position is set to an origin, based on the strength and gradient of the magnetic field detected by the position sensor 31. The predetermined position is assumed to be, for example, a position where the magnetic generator is placed. The position of the ultrasonic probe is defined by a position on a scanning plane (x, y, z) and an rotation angle (θx, θy, θz). The position detection device 32 transmits positional information regarding a calculated position (x, y, z, θx, θy, θz) to the apparatus body 10.

By associating the acquired positional information with ultrasonic image data acquired by ultrasonic waves transmitted and received relative to the ultrasonic probe 70 by time synchronization, etc., the positional information is added to the ultrasonic image data.

The ultrasonic probe 70 includes a plurality of piezoelectric transducers, a matching layer provided to the piezoelectric transducers, and a backing material that prevents propagation of ultrasonic waves to the rear side of the piezoelectric transducers, etc. The ultrasonic probe 70 is detachably connected to the apparatus body 10. The plurality of piezoelectric transducers generate ultrasonic waves based on a driving signal supplied from ultrasonic transmission circuitry 11 provided in the apparatus body 10. The ultrasonic probe 70 may be provided with a button used for offset processing or in case of a freeze, etc. described later. The state of a "freeze" indicates a state where an ultrasonic image is not acquired, for example.

If the ultrasonic probe 70 transmits ultrasonic waves to a subject P, the transmitted ultrasonic waves are sequentially reflected by the boundary showing discontinuity of the acoustic impedance of living tissues of the subject P. The reflected ultrasonic waves by the living tissues are received by the plurality of piezoelectric transducers of the ultrasonic probe 70 as reflected wave signals (echo signals). The amplitude of the received reflected wave signals depends on the difference in the acoustic impedance at the boundary showing discontinuity of the acoustic impedance that affects the reflection of ultrasonic waves. If transmitted ultrasonic pulses are reflected in a bloodstream or on the surface of the cardiac wall, the frequency of the reflected wave signals is shifted depending on velocity components in the direction of transmitting ultrasonic waves in a moving object due to the Doppler effect. The ultrasonic probe 70 receives the reflected wave signals from the subject P, and converts the reflected wave signals into electrical signals. The ultrasonic probe 70 is a 1D array probe in which piezoelectric transducers are arranged in a predetermined direction, a 2D array probe in which piezoelectric transducers are arranged in a two-dimensional matrix form, or a mechanical 4D probe in which piezoelectric transducers are mechanically swept in a direction orthogonal to the direction of transducer arrangement to realize a ultrasonic scan, etc.

The apparatus body 10 generates an ultrasonic image, based on reflected wave signals received by the ultrasonic probe 70. The apparatus body 10 includes the ultrasonic transmission circuitry 11, ultrasonic receive circuitry 12, B-mode processing circuitry 13, Doppler-mode processing circuitry 14, image generation circuitry 15, internal storage circuitry 17, a first memory 18-1 (first cine memory), a second memory 18-2 (second cine memory), an image database 19, an input interface 20, a communication interface 21, and control circuitry 22.

The ultrasonic transmission circuitry 11 is a processor that supplies a driving signal to the ultrasonic probe 70. The ultrasonic transmission circuitry 11 is implemented, for example, by trigger generation circuitry, delay circuitry, pulser circuitry, etc. The trigger generation circuitry repeatedly generates rate pulses for forming transmission ultrasonic waves at a predetermined rate frequency under control of the control circuitry 22. The delay circuitry converges ultrasonic waves generated from the ultrasonic probe 70 as a beam, and applies, to each rate pulse generated by the trigger generation circuitry, a transmission delay time for each ultrasonic transducer required for determining a transmission directivity. The pulser circuitry supplies driving signals (a driving pulse) to the ultrasonic probe 70 at a timing based on the rate pulse under control of the control circuitry 22. By changing the delay time to be applied to each rate pulse from the delay circuitry, the transmission direction from the ultrasonic transducer surface can be discretionarily adjusted.

The ultrasonic receive circuitry 12 is a processor that executes various types of processing on reflected wave signals received by the ultrasonic probe 70 to generate a receive signal. The ultrasonic receive circuitry 12 is implemented, for example, by amplification circuitry, an analog-to-digital (A/D) converter, receive delay circuitry, and an adder, etc. The amplification circuitry executes a gain correction processing for each channel by amplifying reflected wave signals. The A/D converter converts the gain-corrected reflected wave signals into digital signals. The receive delay circuitry delays input of the digital signals to the adder by a delay time required for determining a receive directivity. The adder adds a plurality of digital signals in which the delay time has been applied. After the addition processing of the adder, receive signals are generated in which a reflected component from the direction corresponding to the receive directivity is emphasized.

The B-mode processing circuitry 13 is a processor that generates B-mode data, based on the receive signals received from the ultrasonic receive circuitry 12. The B-mode processing circuitry 13 executes an envelope detection process and a logarithmic amplification process, etc. on the receive signals received from the ultrasonic receive circuitry 12, and generates data (B-mode data) in which the signal intensity is expressed by the brightness intensity. The generated B-mode data is stored in a non-illustrated. RAW data memory as B-mode RAW data on a two-dimensional ultrasonic scanning line.

The Doppler-mode processing circuitry 14 is a processor that generates Doppler spectrum image data and Doppler data, based on the receive signals received from the ultrasonic receive circuitry 12. The Doppler-mode processing circuitry 14 extracts a blood flow signal from the receive signal, generates a Doppler spectrum image data corresponding to a Doppler spectrum image representing a Doppler waveform from the extracted blood flow signal, and generates data (Doppler data) in which information, such as an average speed, dispersion, power, etc. is extracted from the blood flow signal with respect to multiple points. The Doppler waveform is, for example, a waveform in which the blood flow speed within a predetermined range as an observation target is plotted over time. Namely, the Doppler waveform represents a time-series change of the blood flow speed. The generated Doppler data is stored in the non-illustrated RAW data memory as Doppler RAW data on a two-dimensional ultrasonic scanning line.

The image generation circuitry 15 is a processor that is capable of generating various types of ultrasonic image data, based on data generated by the B-mode processing circuitry 13 and the Doppler-mode processing circuitry 14.

The image generation circuitry 15 generates B-mode image data based on B-mode RAW data stored in the RAW data memory. The B-mode image data contains a pixel value (brightness value) that reflects properties of an ultrasonic probe such as convergence of sound waves, or sound-field properties of an ultrasonic beam (for example, transmit/receive beam). In the B-mode image data, for example, the vicinity of a focus portion of ultrasonic waves in a region to be scanned exhibits relatively higher brightness than that of a non-focus portion. The B-mode image based on the B-mode image data represents a form of a structure in the subject P, for example. The image generation circuitry 15 generates B-mode image data in frame units, in accordance with a predetermined frame rate.

The image generation circuitry 15 generates Doppler image data related to an average speed image, a dispersion image, a power image, etc., based on Doppler RAW data stored in the RAW data memory. The image generation circuitry 15 generates Doppler image data in frame units, in accordance with a predetermined frame rate.

In addition, the image generation circuitry 15 performs, to B-mode data stored in the RAW data memory, RAW-voxel conversion which includes an interpolation process taking spatial positional information into consideration to generate B-mode volume data representing form information. The B-mode volume data consists of voxels in a predetermined range. A predetermined pixel value (voxel value) is allocated to each voxel of the B-mode volume data, in accordance with the signal strength of reflected wave signals.

The image generation circuitry 15 performs, to Doppler data stored in the RAW data memory, RAW-voxel conversion which includes an interpolation process taking spatial positional information into consideration to generate blood flow volume data indicating blood flow information. The blood flow volume data consists of voxels in a predetermined range. A predetermined pixel value is allocated to each voxel of the blood flow volume data, in accordance with the direction of blood flow and the blood flow speed.

The image generation circuitry 15 performs, for example, on various types of volume data, a rendering process to generate rendering image data. The image generation circuitry 15 performs, on various types of volume data, an MPR (Multi-Planar Reconstruction) process, to generate MPR image data corresponding to a predetermined cross sectional image (MPR image) in the volume data. The image generation circuitry 15 performs, on the generated various types of volume data, a curved MPR process, to generate curved cross sectional image data corresponding to a predetermined curved cross sectional image in the volume data.

The image generation circuitry 15 executes various types of processes, such as dynamic range, brightness, contrast and y curve corrections, and RGB conversion, etc., to the generated various ultrasonic image data. The image generation circuitry 15 generates ultrasonic image data to be displayed corresponding to an ultrasonic image to be displayed on the display 50, based on a predetermined resolution and display frame rate. The display frame rate is, for example, the number of display frames of an ultrasonic image generated by the image generation circuitry 15 for one second. The display frame rate is basically the same as an acoustic frame rate defined by a scanning cycle of the ultrasonic probe 70 relative to the subject P. The display frame rate may be set to be a fixed value such as 30 frames per second, for example.

The image generation circuitry 15 may generate a GUI (Graphical User Interface) through which an operator (for example, a surgeon) inputs various types of instructions via the input interface 20, and may direct the display 50 to display the GUI. The display 50 may adopt, for example, a CRT display, a liquid crystal display, an organic EL display, an LED display, a plasma display, or any other display known in this technical field. The display 50 has, for example, a function of a notification unit.

The internal storage circuitry 17 includes, for example, a storage medium which is readable by a processor, such as a magnetic or optical storage medium, or a semiconductor memory, etc. The internal storage circuitry 17 stores a control program for implementing ultrasonic transmission/reception, a control program for executing image processing, a control program for executing display processing, etc. The internal storage circuitry 17 stores control programs for implementing various types of functions according to the present embodiment. In addition, the internal storage circuitry 17 stores diagnosis information (e.g., patient ID, doctor's findings, etc.), a diagnosis protocol, a body mark generation program, and data sets such as a conversion table. In the conversion table, color data for use in imaging is associated with each diagnosis region. The internal storage circuitry 17 may store anatomical illustrations, for example, an atlas relating to the structures of internal organs in the living body.

The internal storage circuitry 17 stores various types of ultrasonic image data, volume data, and rendering image data generated by the image generation circuitry 15, in response to an operation input via the input interface 20. The internal storage circuitry 17 may store various types of ultrasonic image data, volume data, and rendering image data generated by the image generation circuitry 15, along with an operation order and an operation time, in response to an operation input via the input interface 20. The internal storage circuitry 17 can transfer the stored data to an external device via the communication interface 21.

The first memory 18-1 includes, for example, a storage medium which is readable by a processor, such as a magnetic or optical storage medium, or a semiconductor memory. The first memory 18-1 stores display image data corresponding to an image (display image) to be displayed on the display 50. In the case where the data amount to be stored in the first memory 18-1 exceeds the storage capacity of the first memory 18-1, data is deleted from the oldest data and new data is stored instead.

For example, the first memory 18-1 stores image data corresponding to a plurality of frames immediately before a freeze operation input through the input interface 20. The freeze operation is to halt acquisition of ultrasonic images. The image data stored in the first memory 18-1 is used for successive display (cine-display), for example. The image data may include ultrasonic image data acquired by an ultrasonic scan, and medical image data acquired by other modalities, such as CT image data, MRI image data, X-ray image data, and nuclear medicine image data, etc.

The second memory 18-2 includes, for example, a storage medium, etc. which is readable by a processor, such as a magnetic or optical storage medium, or a semiconductor memory. The second memory 18-2 stores part of the display image data. Specifically, the image data stored in the second memory 18-2 is part of image data (for example, MPR image data described later) of the display image data stored, for example, in the first memory 18-1. The image data stored in the second memory 18-2 is used for successive display (cine-display), for example.

The image database 19 stores image data transferred from the external device 40. For example, the image database 19 acquires from the external device 40 past image data related to a particular patient acquired by the past diagnosis and stores the acquired image data. The past image data includes ultrasonic image data, CT (Computed Tomography) image data, MR (Magnetic Resonance) image data, PET (Positron Emission Tomography)-CT image data, PET-MR image data, and X-ray image data. For example, the past image data is stored as volume data and rendering image data.

The image database 19 may store a desired image data by reading image data stored in a storage medium such as an MO, a CD-R and a DVD.

The input interface 20 receives various types of instructions from an operator through the input device 60. The input device 60 is, for example, a mouse, a keyboard, a panel switch, a slider switch, a dial switch, a trackball, a rotary encoder, an operation panel, and a touch command screen (TCS), etc. In addition, the input device 60 includes a switch group 61 to switch various types of imaging modes including an ultrasonic wave transmission/reception method, and a receive signal processing method, etc. The switch group 61 may be not only a mechanical device such as a dial switch and/or a trackball, etc., but may also be either an operation panel image displayed on the TCS, or an operation panel image displayed on a second console in the external device 40, etc.

The input interface 20 is connected to the control circuitry 22, for example, via a bus. The input interface 20 converts an operation instruction input by the operator into electric signals, and outputs the electric signals to the control circuitry 22. In the present embodiments, the input interface 20 is not limited to be connected to physical operation components such as a mouse, a keyboard, etc. The input interface 20 may include processing circuitry of electric signals which receives as radio signals from the ultrasonic diagnostic apparatus 1, electric signals corresponding to an operation instruction input from an external input device independently provided, and outputs the electric signals to the control circuitry 22.

The communication interface 21 is, for example, wirelessly connected to the position sensor system 30, and receives positional information transmitted from the position detection device 32. The communication interface 21 is connected to the external device 40 through the network 500, etc., and performs data communication with the external device 40. The external device 40 is, for example, a database of a PACS (Picture Archiving and Communication System) which is a system for managing various types of medical image data, a database of an electronic medical record system for managing electronic medical records which includes medical images, etc. In addition, the external device 40 may, for example, be any medical image diagnostic apparatus other than the ultrasonic diagnostic apparatus 1 according to the present embodiment, such as an X-ray CT apparatus, an MRI (Magnetic Resonance Imaging) apparatus, a nuclear medical diagnostic apparatus, an X-ray diagnostic apparatus, etc. The communication with the external device 40 is performed by using any standards, for example, the DICOM standards.

The control circuitry 22 is a processor acting as a nerve center of the ultrasonic diagnostic apparatus 1, for example. The control circuitry 22 executes a control program stored in the internal storage circuitry 17 to activate a function corresponding to the program. Specifically, the control circuitry 22 has a volume data processing function 221, a display control function 223, and a system control function 225.

The volume data processing function 221 is a function of generating a cross sectional image data for a cross sectional image corresponding to a scanned cross section of an ultrasonic scan from the volume data, based on the positional information of the ultrasonic probe 70. If the volume data processing function 221 is executed, the control circuitry 22 acquires positional information of the ultrasonic probe 70 provided by the position sensor system 30. The control circuitry 22 calculates the scanned cross section of the ultrasonic probe 70 from the acquired positional information. The control circuitry 22 performs MPR processing to the volume data stored, for example, in the image database 19, based on the calculated scanned cross section, and generates MPR image data. The coordinate system for the positional information supplied from the position sensor system 30 and the coordinate system for the volume data stored in the image database 19 are aligned by a predetermined registration method, in advance.

The display control function 223 is a function of displaying on the display 50 an image based on various types of image data. If the display control function 223 is executed, the control circuitry 22 displays on the display 50, for example, an ultrasonic image based on various types of ultrasonic image data generated by the ultrasonic scan, and an MPR image based on MPR image data generated by the volume data processing function 221. Specifically, the control circuitry 22 generates fusion image data based on various types of ultrasonic image data generated by the ultrasonic scan, and MPR image data generated by the volume data processing function 221. A fusion image based on the fusion image data includes an ultrasonic image as a live image acquired in real time by the ultrasonic scan, and an MPR image corresponding to the scanned cross section of the ultrasonic scan. The control circuitry 22 stores the generated fusion image data in the first memory 18-1. The display image and the fusion image (or the display image data and the fusion image data) may be replaced with each other.

The control circuitry 22 generates MPR image data based on the fusion image data stored in the first memory 18-1. The control circuitry 22 stores the generated MPR image data in the second memory 18-2.

The control circuitry 22 may superimpose information related to the ultrasonic image onto the MPR image via the display control function 223, in accordance with various types of imaging modes. Information related to the ultrasonic image may be, for example, a line (or a dotted line) indicating the direction to which ultrasonic waves are emitted, a cursor indicating the direction and a focus of Doppler measurement, a cursor indicating the direction and a gate of Doppler measurement, a line (or a dotted line) indicating the direction of Doppler measurement, a circular marker related to a focus in a CW mode scan, a sample marker indicating a sampling position in a PW mode scan, and an ROI (Region Of Interest) marker, etc.

The system control function 225 is a function of controlling basic operations, such as the input and output, relative to the ultrasonic diagnostic apparatus 1. If the system control function 225 is executed, the control circuitry 22 receives an initiation instruction to initiate various types of imaging modes, via the input interface 20. The various types of imaging modes include, for example, a B-mode, a color Doppler mode, a CW (Continuous Wave) mode, a PW (Pulsed Wave) mode, an M (Motion) mode, and an SWE (Shear Wave Elastography) mode, etc.

The B-mode is an imaging mode in which B-mode image data is generated by a B-mode scan. The color Doppler mode is an imaging mode in which color Doppler image data in which blood flow information acquired using a pulse waveform, for example, is assigned a color by a color Doppler mode scan. The color Doppler mode scan includes a B-mode scan. In the color Doppler mode, both of B-mode image data and color Doppler image data are generated, for example. The color Doppler image based on the color Doppler image data is superimposed on the B-mode image based on the B-mode image data.

The CW mode is an imaging mode in which a Doppler spectrum image data on a scanning line is generated by a CW mode scan (CW type scan) in which, while continuous waves are transmitted, reflected waves are received. In the CW mode, since it is necessary to continuously apply the continuous wave to a target, the B-mode scan cannot be performed.

The PW mode is an imaging mode in which a Doppler spectrum image data related to a particular measurement target position is generated by a PW mode scan (PW type scan) in which pulse waves are transmitted to a scanning line, and reflected waves are received. In the PW mode, the ultrasonic probe generally executes a PW mode scan to a scanning line, but can execute a PW mode scan to a plurality of scanning lines. In this case, the ultrasonic probe sequentially transmits pulse waves to the plurality of scanning lines, and receives reflected waves. In the PW mode, there may be a case where only Doppler spectrum image data is updated to observe a blood flow with a high image quality. In this case, the B-mode scan cannot be performed.

The M-mode is an imaging mode in which M-mode image data, in which brightness images on a line generated from echo data of a targeted scanning line are time-sequentially arranged, is generated by an M-mode scan. In the M-mode, there may be a case where the B-mode scan cannot be performed due to characteristics of the scan.

The SWE mode is an imaging mode which utilizes the property that the propagation speed of shear waves depends on the hardness of tissues in a scanning region. In the SWE mode, push pulses are transmitted to a subject to generate shear waves by transforming part of tissues. The state where the generated shear waves propagate in the tissues is observed by tracking pulses transmitted subsequently to the push pulses, and SWE image data (image data indicating the speed of shear waves or image data indicating the hardness calculated by the speed of the shear waves) is generated. In the SWE mode, since it takes a relatively long time to generate a frame of SWE image data, there may be a case where the B-mode scan cannot be performed.

The B-mode, and the color Doppler mode are examples of a first imaging mode recited in the claims. The CW mode, PW mode, M-mode, and SWE mode are examples of a second imaging mode recited in the claims. The B-mode scan, and the color Doppler mode scan are examples of an ultrasonic scan of a first scanning type recited in the claims. The CW mode scan, PW mode scan, M-mode scan, and SWE mode scan are examples of an ultrasonic scan of a second scanning type recited in the claims.

The control circuitry 22 receives a switching instruction to switch imaging modes, via the input interface 20. For example, the control circuitry 22 receives a switching instruction to switch imaging modes from the color Doppler mode or the B-mode to the CW mode, via the input interface 20. The control circuitry 22 receives a switching instruction to switch imaging modes, for example, from the color Doppler mode or the B-mode to the PW mode, via the input interface 20. The control circuitry 22 receives a switching instruction to switch imaging modes, for example, from the color Doppler mode or the B-mode to the M-mode, via the input interface 20. The control circuitry 22 receives a switching instruction to switch imaging modes, for example, from the B-mode to the SWE mode, via the input interface 20. In the switching instruction, the modes before and after switching may be switched. For example, the control circuitry 22 receives a switching instruction to switch imaging modes from the CW mode to the color Doppler mode or the B-mode.

The volume data processing function 221, the display control function 223, and the system control function 225 may be installed as a control program, or may be installed as hardware circuits specific to respective functions in the control circuitry 22 or in the apparatus body 10 in a manner that the control circuitry 22 can refer to the hardware circuits.

Figure 3:
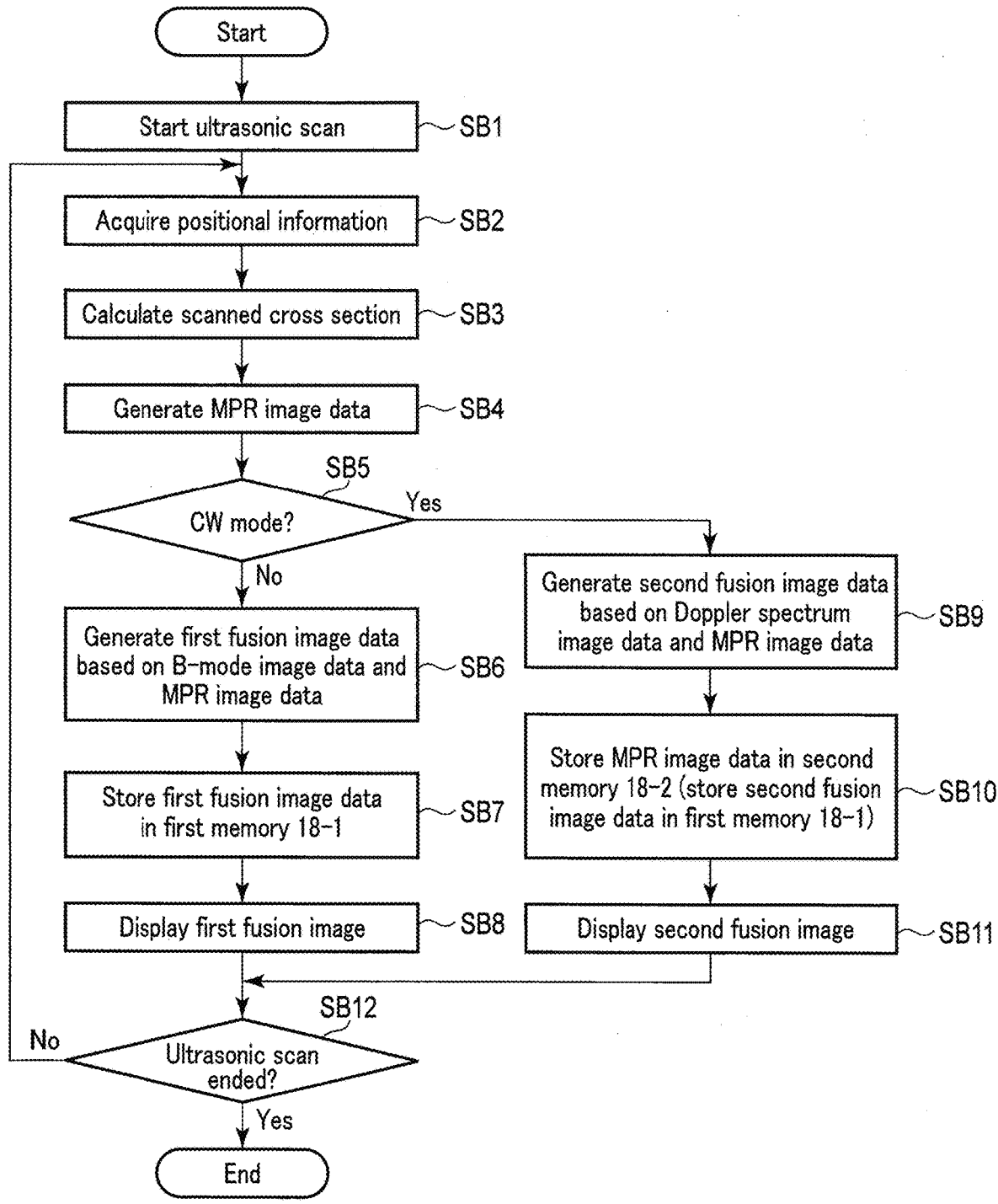
FIG. 3 is a flowchart illustrating the operation in the control circuitry shown in FIG. 1, for generating fusion image data and displaying a fusion image.

Next, the operation of the ultrasonic diagnostic apparatus 1 according to the first embodiment will be explained with reference to the flowcharts shown in FIGS. 2 and 3. FIG. 2 is a flowchart illustrating the operation in control circuitry shown in FIG. 1, when generating Doppler spectrum image data. The operation of the flowchart is implemented by the system control function 225. FIG. 3 is a flowchart illustrating the operation in the control circuitry shown in FIG. 1, for generating fusion image data and displaying a fusion image. The operation of the flowchart is implemented by the volume data processing function 221 and the display control function 223. It is assumed that the coordinate system that defines the position of the ultrasonic probe 70 and the coordinate system that defines a cross sectional position of the pre-acquired volume data are aligned in advance.

First, the flow that the ultrasonic diagnostic apparatus 1 according to the first embodiment performs a CW mode scan will be explained with reference to FIG. 2. In the following description, it is assumed that a CW mode scan is performed after a color Doppler mode scan has been performed. It may be possible that a PW mode scan or an M-mode scan, etc. is performed after a color Doppler mode scan has been performed. It may be possible that a B-mode scan is performed instead of a color Doppler mode scan, and thereafter a PW mode scan or an M-mode scan, etc. is performed.

The control circuitry 22 executes the system control function 225, and receives an initiation instruction to initiate the color Doppler mode scan, via the input interface 20 (step SA1). In this case, the ultrasonic probe 70 is brought into contact with the subject P to be directed to a measurement target position.

Upon receiving the initiation instruction to initiate the color Doppler mode scan, the control circuitry 22 controls the ultrasonic transmission circuitry 11, the ultrasonic receive circuitry 12, the B-mode processing circuitry 13, and the image generation circuitry 15, to perform the color Doppler mode scan (start SA2). Via this processing, the B-mode image data corresponding to a B-mode image in the vicinity of the measurement target position, and the color Doppler image data corresponding to a color Doppler image are generated. The control circuitry 22 combines the generated B-mode image data and color Doppler image data, and generates combined image data. A combined image based on the combined image data is, for example, an image in which a color Doppler image is superimposed onto a B-mode image. The control circuitry 22 directs the display 50 to display the combined image based on the combined image data as a live image. In this case, the operator confirms whether or not the measurement target position is reliably included within the scanning range of the ultrasonic waves, for example, based on the B-mode image. The control circuitry 22 may perform a B-mode scan instead of the color Doppler mode scan. In this case, the control circuitry 22 may generate B-mode image data, and may display a B-mode image based on the B-mode image data on the display 50 as a live image.

After displaying the B-mode image and the color Doppler image on the display 50, the control circuitry 22 receives a setting of a position on the B-mode image where a marker (cursor) that identifies a focus in the CW mode scan is placed (step SA3). If the position of the marker that identifies a focus is determined, the operator inputs an initiation instruction to initiate the CW mode via the input interface 20. The operator may align the B-mode image with the position of the fixed marker.

The control circuitry 22 receives an initiation instruction to initiate the CW mode (step SA4).

Upon receiving the initiation instruction to initiate the CW mode, the control circuitry 22 stops the color Doppler mode scan, and thereafter controls the ultrasonic transmission circuitry 11, the ultrasonic receive circuitry 12, the Doppler-mode processing circuitry 14, and the image generation circuitry 15, to perform the CW mode scan (step SA5). Via this processing, Doppler spectrum image data on a scanning line that includes the position of the marker identifying the set focus is acquired.

Next, the flow that the ultrasonic diagnostic apparatus 1 according to the first embodiment generates fusion image data, and displays a fusion image based on the generated fusion image data on the display 50 will be explained with reference to FIG. 3. In the following description, it is assumed that the generation of fusion image data shown in FIG. 3 is performed in parallel with the ultrasonic scan shown in FIG. 2. Specifically, while performing the processing from step SA1 to step SA3 shown in FIG. 2, the processing from step SB2 to step SB8 is performed in parallel. In addition, while performing the processing from step SA4 to step SA5 shown in FIG. 2, the processing from and step SB2 to step SB5 and the processing from step SB9 to SB11 shown in FIG. 3 are performed in parallel.

The volume data pre-stored in the image database 19 is assumed to be three-dimensional CT image data. The volume data may be ultrasonic image data acquired in the past, or MR image data, PET-CT image data, PET-MR image data, or X-ray image data, etc. acquired by other modalities.

The control circuitry 22 executes the volume data processing function 221, and receives a display instruction to display a fusion image, via the input interface 20 (step SB1). Upon receiving the display instruction to display a fusion image, the control circuitry 22 acquires the positional information of the ultrasonic probe 70 provided from the position sensor system 30 (step SB2).

The control circuitry 22 calculates the scanned cross section of the ultrasonic probe 70 from the acquired positional information (step SB3). The control circuitry 22 performs MPR processing, for example, to the pre-acquired volume data stored in the image database 19, based on the calculated scanned cross section, and generates MPR image data (Step SB4).

The control circuitry 22 determines whether or not the imaging mode is the CW mode (step SB5). If it is determined that the imaging mode is not the CW mode (step SB5: No), namely, in the case where the imaging mode is a color Doppler mode, the control circuitry 22 executes the display control function 223 (step SB6).

By executing the display control function 223, the control circuitry 22 generates fusion image data (first fusion image data) based on the B-mode image data acquired by the color Doppler mode scan, and MPR image data corresponding to the MPR image indicating the scanned cross section of the B-mode image based on the B-mode image data (i.e., the scanned cross section calculated in step SB3). A first fusion image based on the first fusion image data includes at least a B-mode image, and an MPR image corresponding to the B-mode image.

The control circuitry 22 stores the generated first fusion image data in the first memory 18-1 (Step SB7). The control circuitry 22 directs the display 50 to display the first fusion image based on the generated first fusion image data (step SB8).

The control circuitry 22 determines whether or not the ultrasonic scan had ended (step SB12). If it is determined that the ultrasonic scan has not ended (step SB12: No), the control circuitry 22 executes the processing from step SB2 to step SB5 again. If the imaging mode is not switched to the CW mode (step SB5: No), the control circuitry 22 executes the processing from step SB6 to step SB8 again. As described above, in the color Doppler mode, the control circuitry 22 repeats the processing from step SB2 to step SB8, and continues updating the first fusion image displayed on the display 50. The operation of "to continue updating" may be replaced with "to sequentially generate images".

The case where an initiation instruction to initiate the CW mode is input through the input interface 20, via a predetermined operation performed to the switch group 61 included in the input device 60, and the imaging mode is switched from the color Doppler mode to the CW mode, will be explained.

In step SB5 shown in FIG. 3, if the control circuitry 22 determines that the imaging mode is the CW mode (step SB5: Yes), the control circuitry 22 executes the display control function 223.

By executing the display control function 223, the control circuitry 22 generates fusion image data (second fusion image data) based on the Doppler spectrum image data acquired by the CW mode scan, and MPR image data corresponding to the MPR image indicating the scanned cross section indicated by the positional information of the ultrasonic probe 70 when acquiring the Doppler spectrum image data (i.e., the scanned cross section calculated in step SB3) (Step SB9). A second fusion image based on the second fusion image data includes at least a Doppler spectrum image, and an MPR image corresponding to the Doppler spectrum image. If the imaging mode is switched from the color Doppler mode or the B-mode to the M-mode, the second fusion image includes at least an M-mode image based on the M-mode image data generated by the M-mode scan, and an MPR image corresponding to the M-mode image.

The control circuitry 22 stores the generated second fusion image data in the first memory 18-1 (Step SB10). The control circuitry 22 stores the MPR image data used for the second fusion image data in the second memory 18-2. Specifically, the control circuitry 22, for example, extracts the MPR image data from the second fusion image data, and stores the extracted MPR image data in the second memory 18-2.

The control circuitry 22 displays the second fusion image based on the generated second fusion image data on the display 50 (step SB11).

The control circuitry 22 determines whether or not the ultrasonic scan has ended (step SB12). If it is determined that the ultrasonic scan has not ended (step SB12: No), the control circuitry 22 executes the processing from step SB2 to step SB5 and the processing from step SB9 to step SB11 again. As described above, in the CW mode, the control circuitry 22 repeats the processing from step SB2 to step SB5 and the processing from step SB9 to step SB11, and continues updating the second fusion image displayed on the display 50.

If it is determined that the ultrasonic scan has ended (step SB12: Yes), the control circuitry 22 ends updating of the second fusion image (or the first fusion image).

Figure 4:
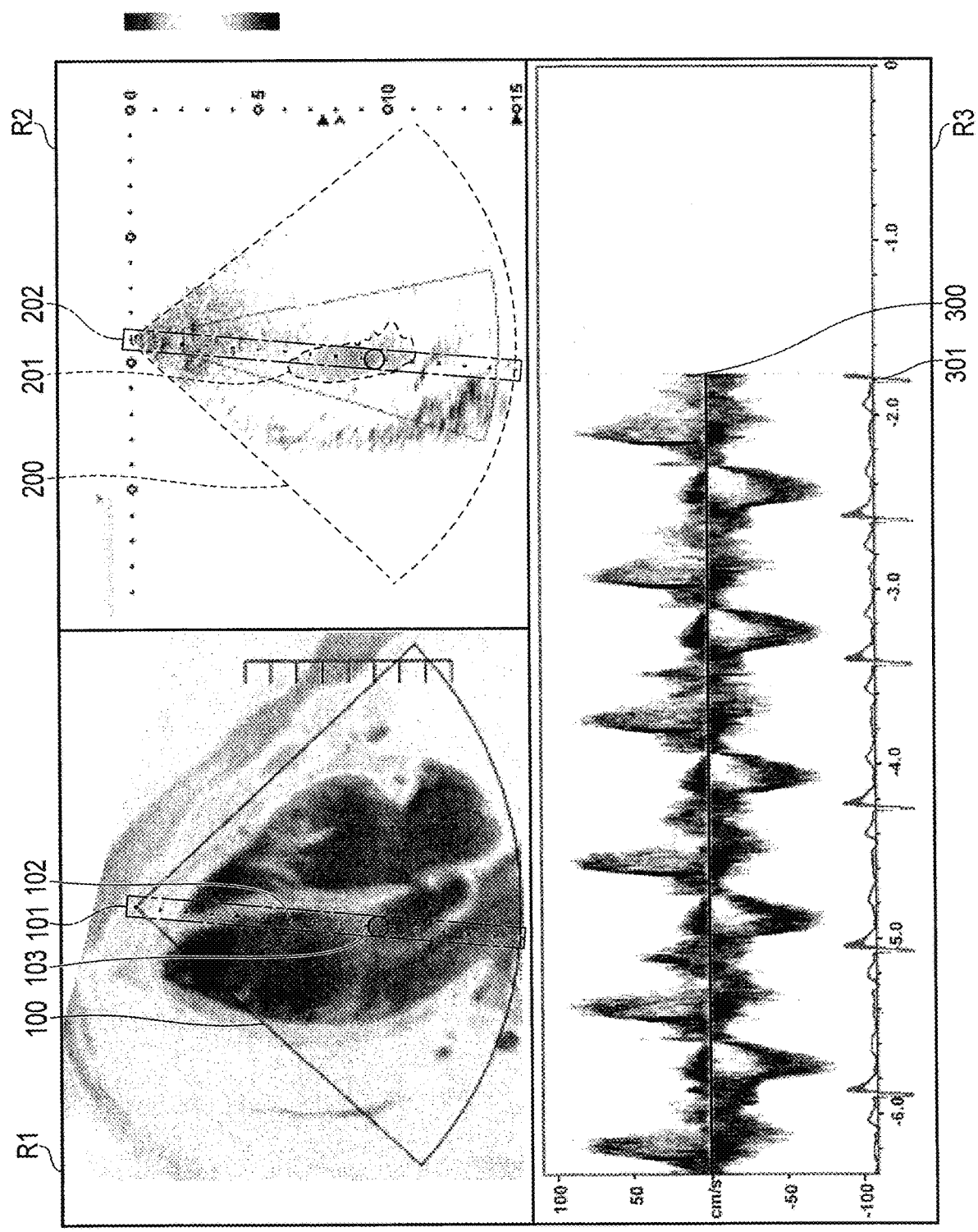
FIG. 4 is an example of a fusion image displayed on a display according to the first embodiment.

FIG. 4 is an example of a fusion image (display image) displayed on the display 50 according to the first embodiment. The display image of FIG. 4 corresponds, for example, to an image while the CW mode scan is performed after the color Doppler mode scan has been performed. The display image of FIG. 4 is divided into, for example, an image region R1, an image region R2, and an image region R3. The display image may be divided into four or more image regions. The images displayed in the image regions may be mutually replaced. This is applicable in the subsequent embodiments.

In the image region R1 of FIG. 4, an MPR image based on the MPR image data generated in step SB4 as shown in. FIG. 3 is displayed. The operator views the MPR image and can recognize the acquisition position of the echo data when the B-mode image is not acquired.

A scanning range 100 and a cursor 101 are superimposed on the MPR image. The scanning range 100 indicates a rendering range of the B-mode image based on the position of the ultrasonic probe 70. The cursor 101 indicates the direction and the focus of the Doppler measurement in the CW mode scan. Specifically, the cursor 101 is indicated by a line 102 indicating the direction of the Doppler measurement and a circular marker 103 positioned on the line 102. The center of the circular marker 103 indicates, for example, the focus in the CW mode scan. The position of the cursor 101 is calculated based on the positional information of the ultrasonic probe 70 acquired during the CW mode scan.

A B-mode image 200 is displayed in the image region R2 of FIG. 4. A color Doppler image 201 and a cursor 202 are superimposed on the B-mode image 200. The cursor 202 is similar to the cursor 101. The B-mode image 200 corresponds to a B-mode image based on the B-mode image data acquired immediately before the color Doppler mode scan is stopped.

A Doppler spectrum image 300 and an ECG (Electro Cardio Graph) waveform 301 are displayed in the image region R3 of FIG. 4. The Doppler spectrum image 300 is acquired, for example, by the CW mode scan. The ECG waveform is generated based on ECG waveform data acquired synchronized with the Doppler spectrum image 300 in the time axis. The ECG waveform data is acquired, for example, by a non-illustrated electrocardiograph provided in the ultrasonic diagnostic apparatus 1. The electrocardiograph is, for example, a measurement device that detects electric signals synchronized with a heartbeat that are emitted from the electrodes attached to the subject P on which the CW mode scan is performed. The ECG waveform is an example of a biological waveform obtained by graphing biological information, and may be replaced with a waveform based on other biological signals of the subject P having periodicity, for example, a respiration waveform, etc. In addition, it may be possible that in response to an operation of designating a time phase on the ECG waveform, an MPR image corresponding to the designated time phase is read from the second memory 18-2.

The MPR image data stored in the second memory 18-2 is referred to when the Doppler spectrum image is independently confirmed in the time sequence at the time of setting of an image quality change, and after the CW mode scan has ended. For example, it may be possible that in response to an operation of designating a time phase on the Doppler spectrum image, an MPR image corresponding to the designated time phase is read from the second memory 18-2. In the case where the imaging mode is switched from the color Doppler mode or the B-mode to the M-mode, it may be possible that in response to an operation of designating a time phase on the M-mode image based on the M-mode image data generated by the M-mode scan, an MPR image corresponding to the designated time phase is read from the second memory 18-2.

As described above, according to the first embodiment, the control circuitry 22 receives a switching instruction to switch imaging modes from the color Doppler mode to the CW mode, via the input interface 20. The control circuitry 22 controls the ultrasonic transmission circuitry 11, the ultrasonic receive circuitry 12, and the B-mode processing circuitry 13 to generate a receive signal by the color Doppler mode scan in the color Doppler mode. The control circuitry 22 controls the ultrasonic transmission circuitry 11, and the ultrasonic receive circuitry 12 to generate a receive signal by the CW mode scan in the CW mode. The control circuitry 22 sequentially generates B-mode image data based on receive signals generated in the color Doppler mode. In addition, the control circuitry 22 sequentially generates Doppler spectrum image data based on the generated receive signals in the CW mode. The control circuitry 22 executes the volume data processing function 221, and sequentially generates MPR image data from the volume data (for example, CT image data) pre-stored in the image database 19, based on the positional information of the ultrasonic probe 70 provided from the position sensor system 30. The control circuitry 22 sequentially displays the first fusion images that include a B-mode image and an MPR image corresponding to the B-mode image on the display 50 in the color Doppler mode. The control circuitry 22 sequentially displays the second fusion images that include a Doppler spectrum image and an MPR image corresponding to the Doppler spectrum image on the display 50 in the CW mode.

Via this processing, the operator can view the sequentially updated MPR image even in the case where the B-mode scan cannot be performed during the CW mode scan, for example. The MPR image is an image morphologically indicating tissues, similar to the B-mode image. Accordingly, it is possible to recognize the position of the ultrasonic probe 70 based on the morphological structure included in the displayed MPR image.

Thus, it is possible to assist recognition of the acquisition position of the echo data when the B-mode image is not acquired.

Second Embodiment

In the first embodiment, the control circuitry 22 can recognize the acquisition position of the echo data, for example, when the B-mode image is not acquired, by continuously displaying the MPR image corresponding to the position of the ultrasonic probe 70 in real time. In the second embodiment, the case where the positional shift of the ultrasonic probe 70 after switching the modes is notified, in addition to continuously displaying the MPR image corresponding to the position of the ultrasonic probe 70 in real time, will be described.

Figure 5:
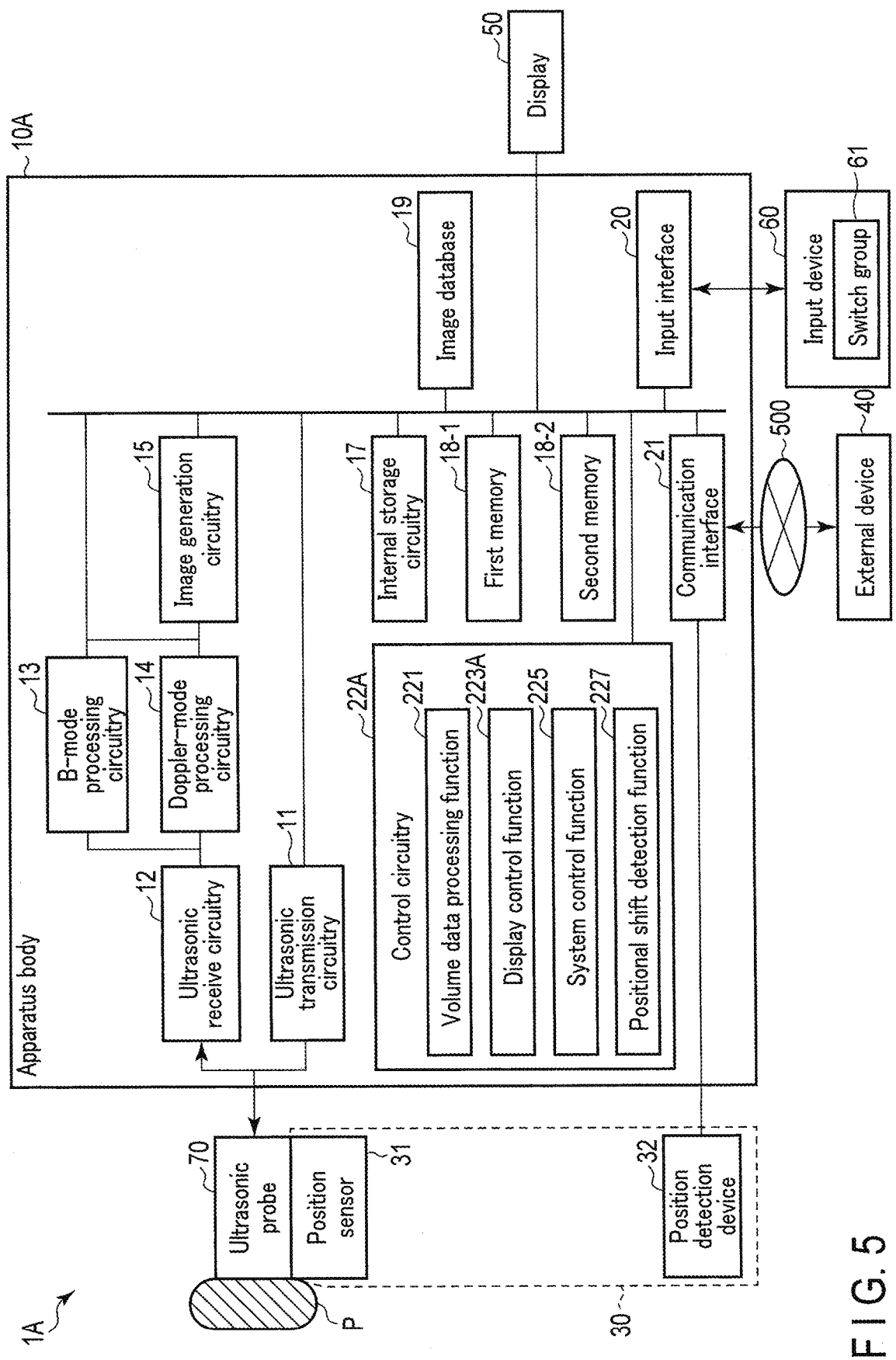
FIG. 5 illustrates an example configuration of an ultrasonic diagnostic apparatus according to the second embodiment.

As shown in FIG. 5, the ultrasonic diagnostic apparatus 1A includes an apparatus body 10A, the ultrasonic probe 70, the position sensor system 30, the display 50, and the input device 60. The apparatus body 10A is connected to the external device 40 via the network 500. The apparatus body 10A is also connected to a position sensor system 30, the display 50, and the input device 60.

The apparatus body 10A generates an ultrasonic image, based on reflected wave signals received by the ultrasonic probe 70. The apparatus body 10A includes the ultrasonic transmission circuitry 11, the ultrasonic receive circuitry 12, the B-mode processing circuitry 13, the Doppler-mode processing circuitry 14, the image generation circuitry 15, the internal storage circuitry 17, the first memory 18-1 (first cine memory), the second memory 18-2 (second cine memory), the image database 19, the input interface 20, the communication interface 21, and control circuitry 22A.

The control circuitry 22A is a processor acting as a nerve center of the ultrasonic diagnostic apparatus 1A, for example. The control circuitry 22A executes a control program stored in the internal storage circuitry 17 to activate a function corresponding to the program. Specifically, the control circuitry 22A has the volume data processing function 221, a display control function 223A, the system control function 225, and a positional shift detection function 227.

The positional shift detection function 227 is a function of detecting the positional shift of the ultrasonic probe 70 based on the positional information when switching the modes, acquired by the position sensor 31 provided in the ultrasonic probe 70, and the positional information after switching the mode. The positional shift is a focal shift of ultrasonic waves transmitted from the ultrasonic probe 70, caused by the positional shift of the ultrasonic probe 70, for example, after switching the modes. The focal position of the ultrasonic waves is a central position of a sample gate set before performing the PW mode scan, for example. The sample gate is a marker to designate a position where the Doppler spectrum image is measured.

Specifically, if the positional shift detection function 227 is executed, the control circuitry 22A acquires a focal position of ultrasonic waves set before the PW mode scan is performed, for example. The control circuitry 22A calculates the focal position of the ultrasonic waves based on the positional information of the ultrasonic probe 70, acquired during the PW mode scan. The control circuitry 22A calculates a difference between the focal position of ultrasonic waves immediately before the B-mode scan is ended and the calculated focal position of ultrasonic waves, for example, a distance in the Euclidean space. Via this process, the positional shift is detected.

The display control function 223A includes a function of notifying the positional shift of the ultrasonic probe 70 from the position at the time when the B-mode scan ends in the PW mode scan, in addition to the function of the display control function 223 according to the first embodiment. By executing the display control function 223A, the control circuitry 22A generates guide image data indicating the degree of positional shift, based on the positional shift detected by the positional shift detection function 227, for example. A guide image based on the guide image data includes, for example, the distance in the Euclidean space calculated by the positional shift detection function 227. In addition, the control circuitry 22A generates fusion image data (third fusion image data) based on the Doppler spectrum image data generated during the PW mode scan, the MPR image data generated by the volume data processing function 221, and the generated guide image data.

A third fusion image based on the third fusion image data includes a Doppler spectrum image acquired in real time by the PW mode scan, an MPR image corresponding to the scanned cross section at the time of acquiring the Doppler spectrum image, and the guide image. The control circuitry 22A stores the generated third fusion image data in the first memory 18-1. The control circuitry 22A also stores the MPR image data and the guide image data used for generation of the third fusion image data in the second memory 18-2. Information of the guide image data may be superimposed onto the MPR image data stored in the second memory 18-2.

Figure 6:
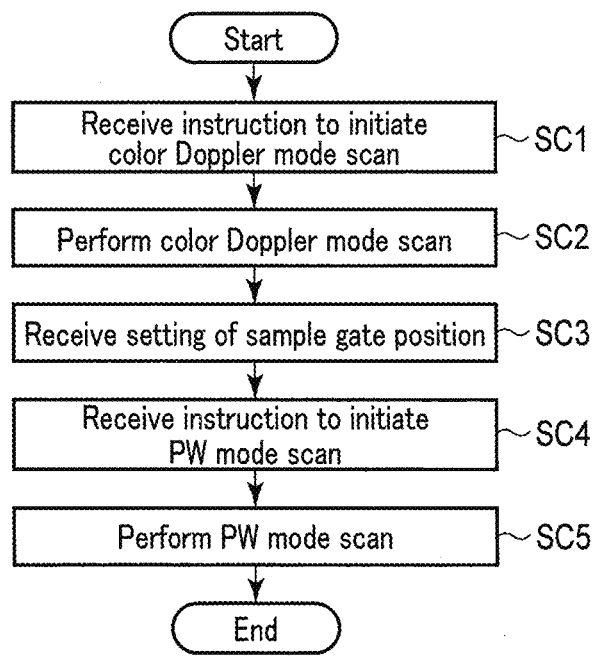
FIG. 6 is a flowchart illustrating the operation in control circuitry shown in FIG. 5 when generating Doppler spectrum image data.
Figure 7:
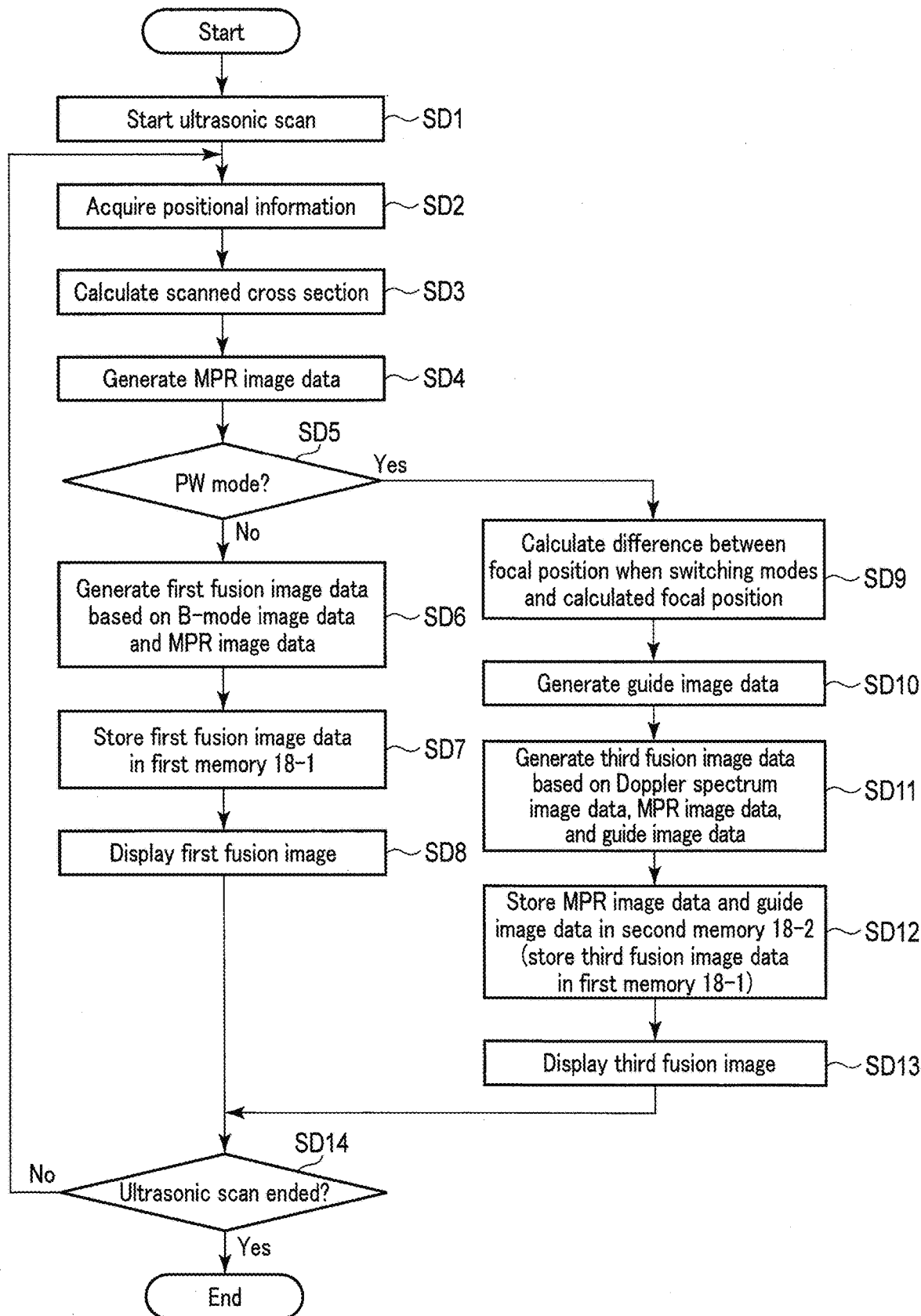
FIG. 7 is a flowchart illustrating the operation in the control circuitry shown in FIG. 5, for generating fusion image data and displaying a fusion image.

Next, the operation of the ultrasonic diagnostic apparatus 1A according to the second embodiment will be explained with reference to the flowcharts shown in FIGS. 6 and 7. FIG. 6 is a flowchart illustrating the operation in control circuitry shown in FIG. 5, for generating Doppler spectrum image data. The operation of the flowchart is implemented by the system control function 225. FIG. 7 is a flowchart illustrating the operation in the control circuitry shown in FIG. 5, for generating fusion image data and displaying a fusion image. The operation of the flowchart is implemented by the volume data processing function 221, the display control function 223A, and the positional shift detection function 227.

First, the flow of a PW mode scan that the ultrasonic diagnostic apparatus 1A according to the second embodiment performs will be explained with reference to FIG. 6. In the following description, it is assumed that a PW mode scan is performed after a color Doppler mode scan has been performed. In this case, it is assumed that the number of the measurement target positions of the PW mode scan is one. It may be possible that a CW mode scan or an M-mode scan, etc. is performed after the color Doppler mode scan has been performed. It may also be possible that a B-mode scan is performed instead of a color Doppler mode scan, and thereafter a CW mode scan or an M-mode scan, etc. is performed.

Since the processing in steps SC1 and SC2 is the same as the processing in steps SA1 and SA2 of FIG. 2, the explanations thereof will be omitted.

After displaying the B-mode image and the color Doppler image on the display 50, the control circuitry 22A receives a setting of a position on the B-mode image where a marker (cursor) that is referred to as a sample gate is placed (step SC3). If the position of the sample gate is determined, the operator inputs an initiation instruction to initiate the PW mode via the input interface 20.

The control circuitry 22A receives an initiation instruction to initiate the PW mode (step SC4). Upon receiving the initiation instruction to initiate the PW mode, the control circuitry 22A stops the color Doppler mode scan, and thereafter controls the ultrasonic transmission circuitry 11, the ultrasonic receive circuitry 12, the Doppler-mode processing circuitry 14, and the image generation circuitry 15, to perform the PW mode scan (step SC5). Via this processing, Doppler spectrum image data at the position of the set sample gate is acquired.

Next, the flow in which the ultrasonic diagnostic apparatus 1A according to the second embodiment generates fusion image data, and displays a fusion image based on the generated fusion image data on the display 50 will be explained with reference to FIG. 7. In the following description, it is assumed that the generation of fusion image data shown in FIG. 7 is performed in parallel with the ultrasonic scan shown in FIG. 6. Specifically, while performing the processing from step SC1 to step SC3 shown in FIG. 6, the processing from step SD2 to step SD8 shown in FIG. 7 is performed in parallel. In addition, while performing the processing from step SC4 to step SC5 shown in FIG. 6, the processing from and step SD2 to step SD5, and the processing from step SD9 to SD13 shown in FIG. 7 are performed in parallel.

Since the processing from steps SD1 to SD4 is the same as the processing from in steps SB1 and SB4 of FIG. 3, the explanations thereof will be omitted.

The control circuitry 22A determines whether or not the imaging mode is the PW mode (step SD5). If it is determined that the imaging mode is not the PW mode (step SD5: No), namely, in the case where the imaging mode is a color Doppler mode, the control circuitry 22A executes the display control function 223A (step SD6).

Since the processing from steps SD7 and SD8 shown in FIG. 7 is the same as the processing from in steps SB7 and SB8 of FIG. 3, the explanations thereof will be omitted.

The case where an initiation instruction to initiate the PW mode is input through the input interface 20, and the imaging mode is switched from the color Doppler mode to the PW mode will be explained.

In step SD5 shown in FIG. 7, if the control circuitry 22A determines that the imaging mode is the PW mode (step SD5: Yes), the control circuitry 22A executes the positional shift detection function 227 (step SD9).

Specifically, if the positional shift detection function 227 is executed, the control circuitry 22A acquires a focal position of ultrasonic waves set before the PW mode scan is performed. The control circuitry 22A calculates the focal position of the ultrasonic waves based on the positional information of the ultrasonic probe 70, acquired during the PW mode scan. The control circuitry 22A calculates a difference between the focal position of ultrasonic waves immediately before the color Doppler mode scan is stopped and the calculated focal position of ultrasonic waves, for example, a distance in the Euclidean space (Step SD9). Via this process, the positional shift is detected.

If the positional shift is detected, the control circuitry 22A executes the display control function 223A, and generates guide image data based on the calculated distance in the Euclidean space (step SD10).

The control circuitry 22A generates third fusion image data based on the Doppler spectrum image data generated during the PW mode scan, the MPR image data generated in step SD4 shown in FIG. 7, and the generated guide image data (step SD11). A third fusion image based on the third fusion image data includes at least a Doppler spectrum image, an MPR image corresponding to the Doppler spectrum image, and a guide image based on the guide image data generated in step SD10.

The control circuitry 22A stores the generated third fusion image data in the first memory 18-1 (Step SD12). The control circuitry 22A stores the MPR image data and the guide image data used for generation of the third fusion image data in the second memory 18-2. Specifically, the control circuitry 22A extracts the MPR image data on which the guide image data is superimposed from the third fusion image data, and stores the extracted MPR image data in the second memory 18-2.

The control circuitry 22A displays the third fusion image based on the generated third fusion image data on the display 50 (step SD13).

The control circuitry 22A determines whether or not the ultrasonic scan has ended (step SD14). If it is determined that the ultrasonic scan has not ended (step SD14: No), the control circuitry 22A executes the processing from step SD2 to step SD5 and the processing from step SD9 to step SD13 again. As described above, in the PW mode, the control circuitry 22A repeats the processing from step SD2 to step SD5 and repeats the processing from step SD9 to step SD11, and continues updating the third fusion image displayed on the display 50.

If it is determined that the ultrasonic scan has ended (step SD14: Yes), the control circuitry 22 ends updating of the third fusion image (or the first fusion image).

Figure 8:
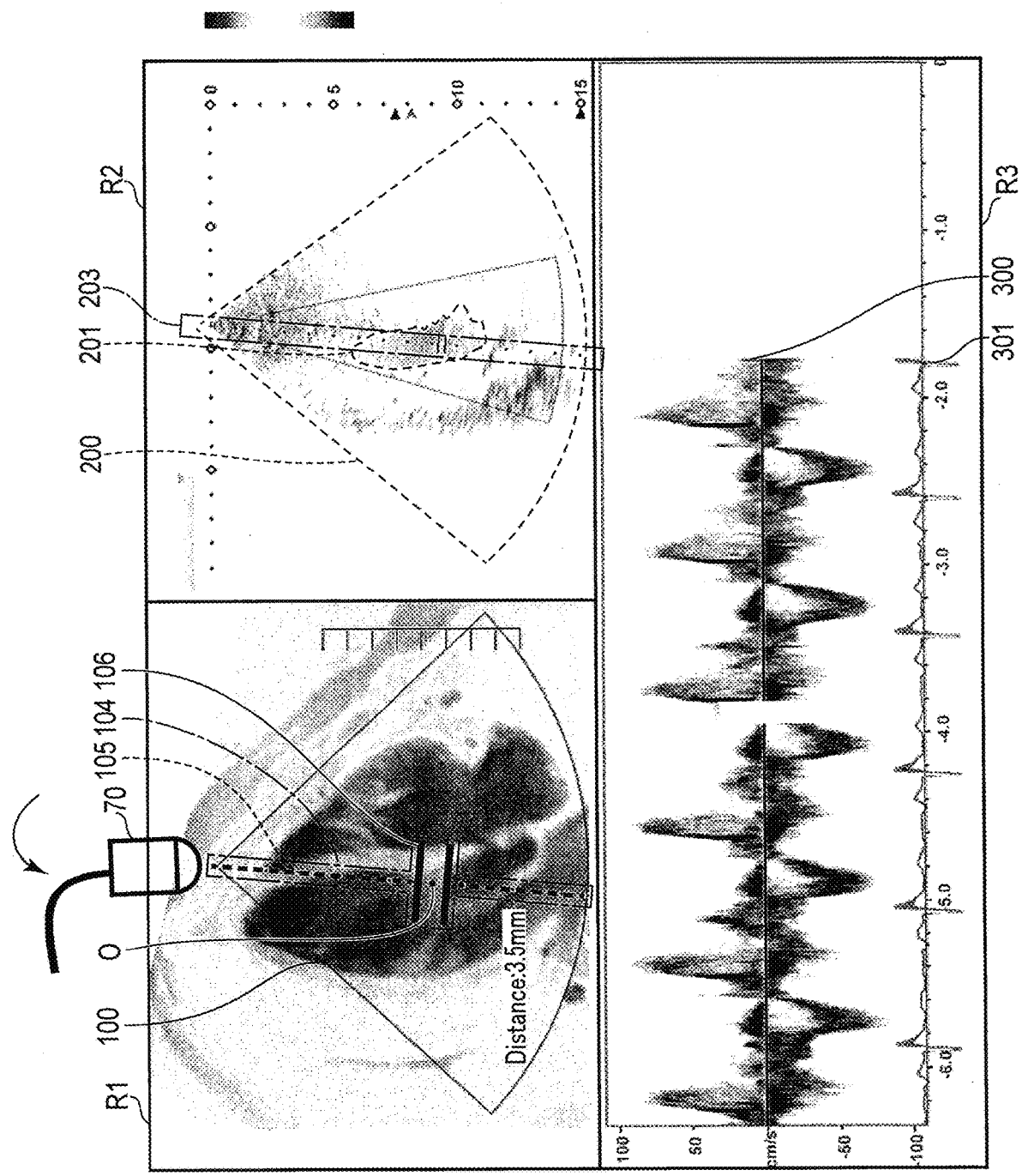
FIG. 8 is an example of a fusion image displayed on the display according to the second embodiment.

FIG. 8 is an example of a fusion image (display image) displayed on the display 50 according to the second embodiment. The display image of FIG. 8 corresponds, for example, to an image while the PW mode scan is performed after the color Doppler mode scan has been performed. The display image of FIG. 8 is divided into, for example, an image region R1, an image region R2, and an image region R3.

In the image region R1 of FIG. 8, an MPR image based on the MPR image data generated in step SD4 as shown in FIG. 7 is displayed. The operator views the MPR image and can recognize the acquisition position of the echo data when the B-mode image is not acquired.

A scanning range 100 and a cursor 104 (Doppler cursor) are superimposed on the MPR image. The cursor 104 indicates the direction and the gate of the pulse Doppler measurement in the PW mode scan. Specifically, the cursor 104 is indicated by a line 105 indicating the direction of the pulse Doppler measurement and a gate 106 represented by a pair of short lines (double lines) and indicating a measurement target position. The position of the cursor 104 is calculated based on the positional information of the ultrasonic probe 70 acquired during the PW mode scan.

In addition, text "Distance: 3.5 mm" is superimposed onto the MPR image, for example. The text "Distance: 3.5 mm" is displayed to notify the operator who is viewing the display 50 of the occurrence of a positional shift of the ultrasonic probe 70. The value "3.5 mm" indicates the distance in the Euclidean space calculated by the control circuitry 22A in step SD9 shown in FIG. 7. The value "3.5 mm" indicates, for example, the distance from the center O of the gate 106. The text "Distance: 3.5 mm" and the gate 106 shown in FIG. 8 are assigned a predetermined display color in accordance with the calculated distance in the Euclidean space. The display color may be yellow, for example. The operator can recognize the degree of the positional shift based on the display color.

The control circuitry 22A may display a first sample gate set before the PW mode scan is initiated and a second sample gate based on the position calculated based on the positional information of the ultrasonic probe 70 acquired during the PW mode scan in parallel. In this case, the control circuitry 22A assigns a predetermined display color to the first sample gate, for example. The control circuitry 22A assigns to the second sample gate a display color different from that assigned to the first sample gate, in accordance with the calculated distance in the Euclidean space.

A B-mode image 200 is displayed in the image region R2 of FIG. 8. A color Doppler image 201 and a cursor 203 are superimposed on the B-mode image 200. The cursor 203 is similar to the cursor 104. The B-mode image 200 corresponds, for example, to a B-mode image based on the B-mode image data acquired immediately before the color Doppler mode scan is stopped.

A Doppler spectrum image 300 and an ECG waveform 301 are displayed in the image region R3 of FIG. 8. The Doppler spectrum image 300 is acquired, for example, by the PW mode scan.

As described above, according to the second embodiment, the control circuitry 22A receives a switching instruction to switch imaging modes from the color Doppler mode to the PW mode, via the input interface 20. The control circuitry 22A controls the ultrasonic transmission circuitry 11 and the ultrasonic receive circuitry 12 to generate a receive signal by the color Doppler mode scan in the color Doppler mode. The control circuitry 22A controls the ultrasonic transmission circuitry 11 and the ultrasonic receive circuitry 12 to generate a receive signal by the PW mode scan in the PW mode. The control circuitry 22A sequentially generates B-mode image data based on B-mode data generated in the color Doppler mode. The control circuitry 22A sequentially generates Doppler spectrum image data based on the generated Doppler data in the PW mode. During the PW mode scan, the control circuitry 22A executes the positional shift detection function 227, and detects the positional shift of the ultrasonic probe 70 based on the positional information of the ultrasonic probe 70 immediately before the color Doppler mode scan is stopped and the positional information of the ultrasonic probe 70 during PW mode scan. The control circuitry 22A executes the display control function 223A, and displays on the display 50 the detected positional shift as a distance in the Euclidean space.

Via this processing, the operator can clearly recognize the occurrence of the positional shift of the ultrasonic probe 70 when the B-mode image is not acquired.

Other Embodiments

In the first embodiment, the control circuitry 22 stores the MPR image data generated during the CW mode scan in the second memory 18-2; however, the embodiments are not limited thereto. For example, upon receiving an initiation instruction to initiate the CW mode, the control circuitry 22 may generate MPR image data based on the first fusion image data stored in the first memory 18-1 during the color Doppler mode scan, and may store the MPR image data in the second memory 18-2. Via this processing, the MPR image data generated before switching the imaging modes can be referred to when the operator desires to view only an MPR image.

Figure 9:
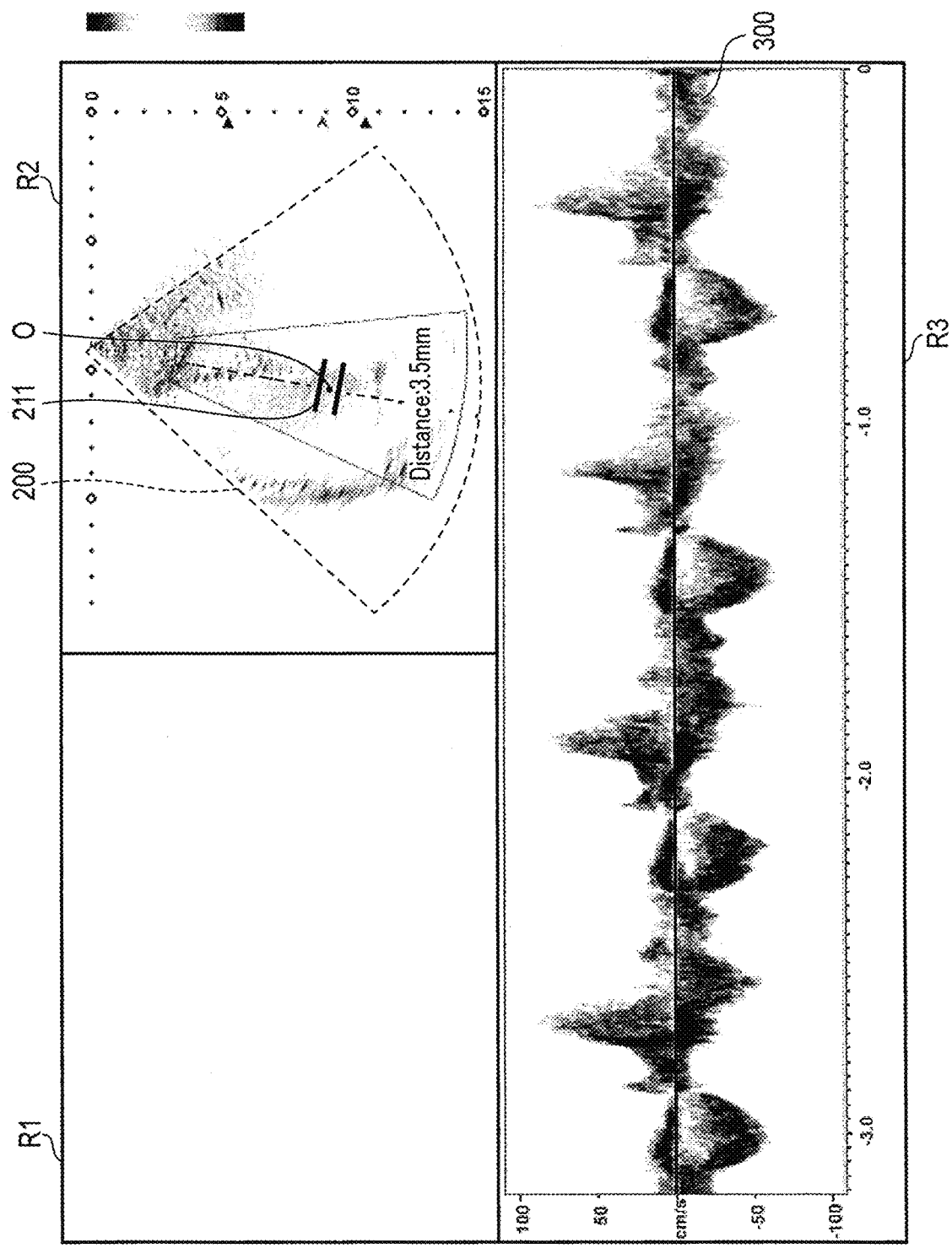
FIG. 9 is an example of a fusion image displayed on a display according to another embodiment.

In the second embodiment, the control circuitry 22A generates MPR image data based on the positional information of the ultrasonic probe 70, but the embodiments are not limited thereto. The control circuitry 22A, for example, may notify the positional shift only by the guide image, without generating MPR image data. Specifically, the control circuitry 22A, for example, displays the text "Distance: 3.5 mm" and a sample gate 211 superimposed onto the B-mode image 200 displayed in the image region R2 as shown in FIG. 9. FIG. 9 is an example of a fusion image displayed on the display 50 according to another embodiment. In this case, the control circuitry 22A does not display anything in the image region R1, as shown in FIG. 9. Accordingly, it is possible to decrease the load due to generation of MPR image data.

Figure 10:
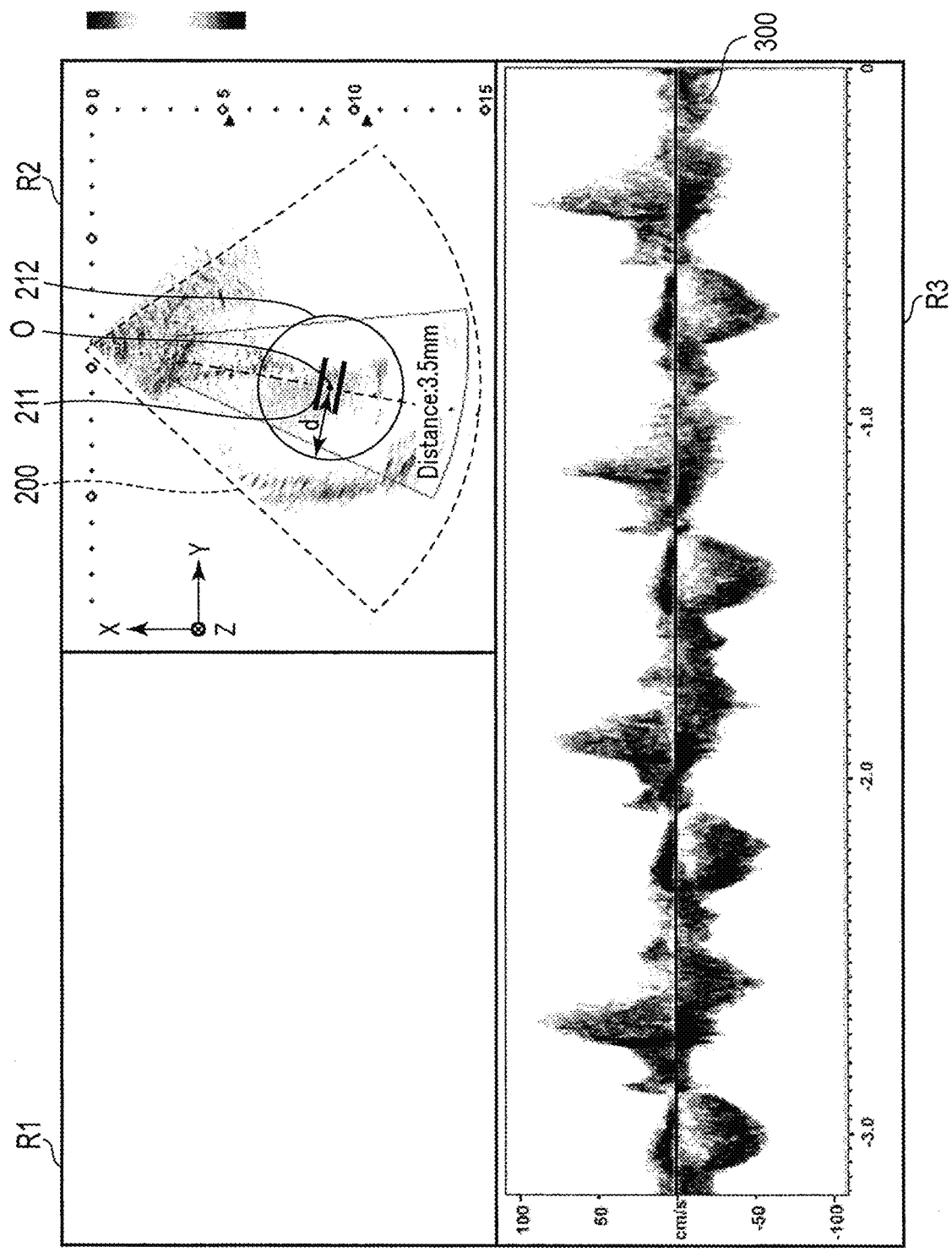
FIG. 10 is an example of a fusion image displayed on a display according to another embodiment.

In the second embodiment, the control circuitry 22A displays the distance in the Euclidean space as text with respect to the positional shift; however, the embodiments are not limited thereto. The control circuitry 22A may, for example, display a plan-view image which indicates the shift amount in the depth direction in the image region R2, as shown in FIG. 10. FIG. 10 is an example of a fusion image displayed on the display 50 according to another embodiment. As shown in FIG. 10, the control circuitry 22A, for example, displays a circle 212 which is a group of points away from the center O of the sample gate 211 by a predefined distance "d". The operator can recognize, for example, the positional shift by the predetermined distance d from the center O in the depth direction (Z-direction), as shown in FIG. 10.

In the second embodiment, the control circuitry 22A, for example, transmits pulse waves to a scanning line, and receives the reflected waves to generate the Doppler spectrum image data in the PW mode scan; however, the embodiments are not limited thereto. For example, the control circuitry 22A may sequentially transmit pulse waves to a plurality of scanning lines, and receives the reflected waves to generate the Doppler spectrum image data in the PW mode scan. For example, the control circuitry 22A alternately transmits pulse waves to a first measurement target position and a second measurement target position placed in the different scanning lines, and receives the reflected waves. Via this processing, the control circuitry 22A can generate the Doppler spectrum image data at the two measurement target positions, and can simultaneously display Doppler spectrum images based on the Doppler spectrum image data generated for the two measurement target positions.

By the way, the control circuitry 22, for example, performs MPR processing to volume data corresponding to one time phase, and generates MPR image data, in step SB4 of FIG. 3. However, the embodiments are not limited thereto. The control circuitry 22, for example, may perform MPR processing to the volume data corresponding to each of multiple time phases, and may generate MPR image data. In this case, the control circuitry 22 switches volume data based on which the MPR image data is generated, synchronized with the biological waveform. Specifically, the control circuitry 22 generates MPR image data synchronized with the cardiac time phases during the PW mode scan, based not only on the positional information of the ultrasonic probe 70, but also on, for example, ECG waveform data acquired synchronized with the volume data acquisition, and ECG waveform data acquired in parallel with the PW mode scan, and switches the display of MPR images.

In the aforementioned embodiments, the control circuitry 22, for example, displays an MPR image based on the CT image data on the display 50, as shown in FIG. 4; however, the embodiments are not limited thereto. The control circuitry 22, for example, may display a plurality of MPR images generated respectively from multiple items of volume data acquired by different modalities on the display 50.

In the aforementioned embodiments, a receive signal generated by the ultrasonic receive circuitry 12 via the B-mode scan and the color Doppler mode scan is an example of first echo data recited in the claims. A receive signal generated by the ultrasonic receive circuitry 12 via the CW mode scan, the PW mode scan, the M-mode scan, and PWE mode scan is an example of second echo data recited in the claims. A B-mode image, and a combined image in which a B-mode image and a color Doppler image are combined are an example of a first image recited in the claims. A Doppler spectrum image, an M-mode image, and an elastic image based on elastic image data are an example of a second image recited in the claims. An MPR image is an example of a third image recited in the claims.

Display Examples

Figure 11:
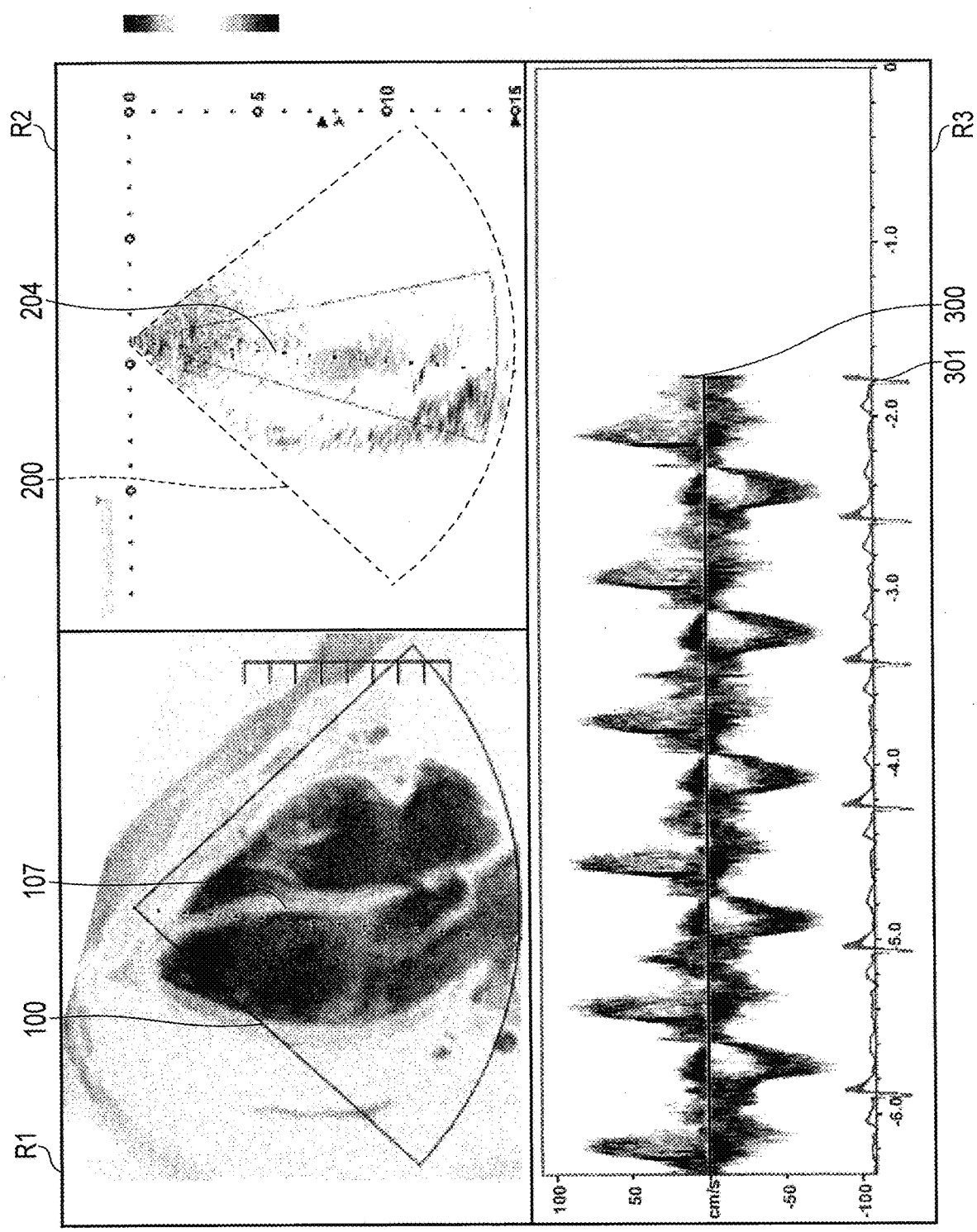
FIG. 11 is an example of a fusion image displayed on the display according to another embodiment.

FIG. 11 is an example of a fusion image (display image) displayed on a display according to another embodiment. The display image of FIG. 11 corresponds to an image while the CW mode scan is performed after the B-mode scan has been performed. The display image of FIG. 11 is divided into, for example, an image region R1, an image region R2, and an image region R3. The display image of FIG. 11 is different from the display image of FIG. 4 in that a circular marker is not displayed.

A B-mode image 200 is displayed in the image region R2. A cursor 204 is superimposed on the B-mode image 200. The cursor 204 indicates the direction to which ultrasonic waves are emitted in the CW mode. A combined image in which a color Doppler image is combined with the B-mode image may be displayed in the image region R2.

An MPR image is displayed in the image region R1. A scanning range 100 and a cursor 107 are superimposed on the MPR image. The cursor 107 is similar to the cursor 204. The position of the cursor 107 is calculated, for example, based on the positional information of the ultrasonic probe 70 acquired during the CW mode scan.

A Doppler spectrum image 300 and an ECG waveform 301 are displayed in the image region R3. The Doppler spectrum image 300 is acquired, for example, by the CW mode scan.

In sum, the display image of FIG. 11 includes a fusion image in which at least an MPR image and a B-mode image are simultaneously displayed, and a fusion image in which at least an MPR image and a Doppler spectrum image are simultaneously displayed. A cursor 107 is constantly displayed on the MPR image. Since the cursor 107 is constantly displayed on the MPR image, an operator can constantly recognize the acquisition position of the echo data.

Figure 12:
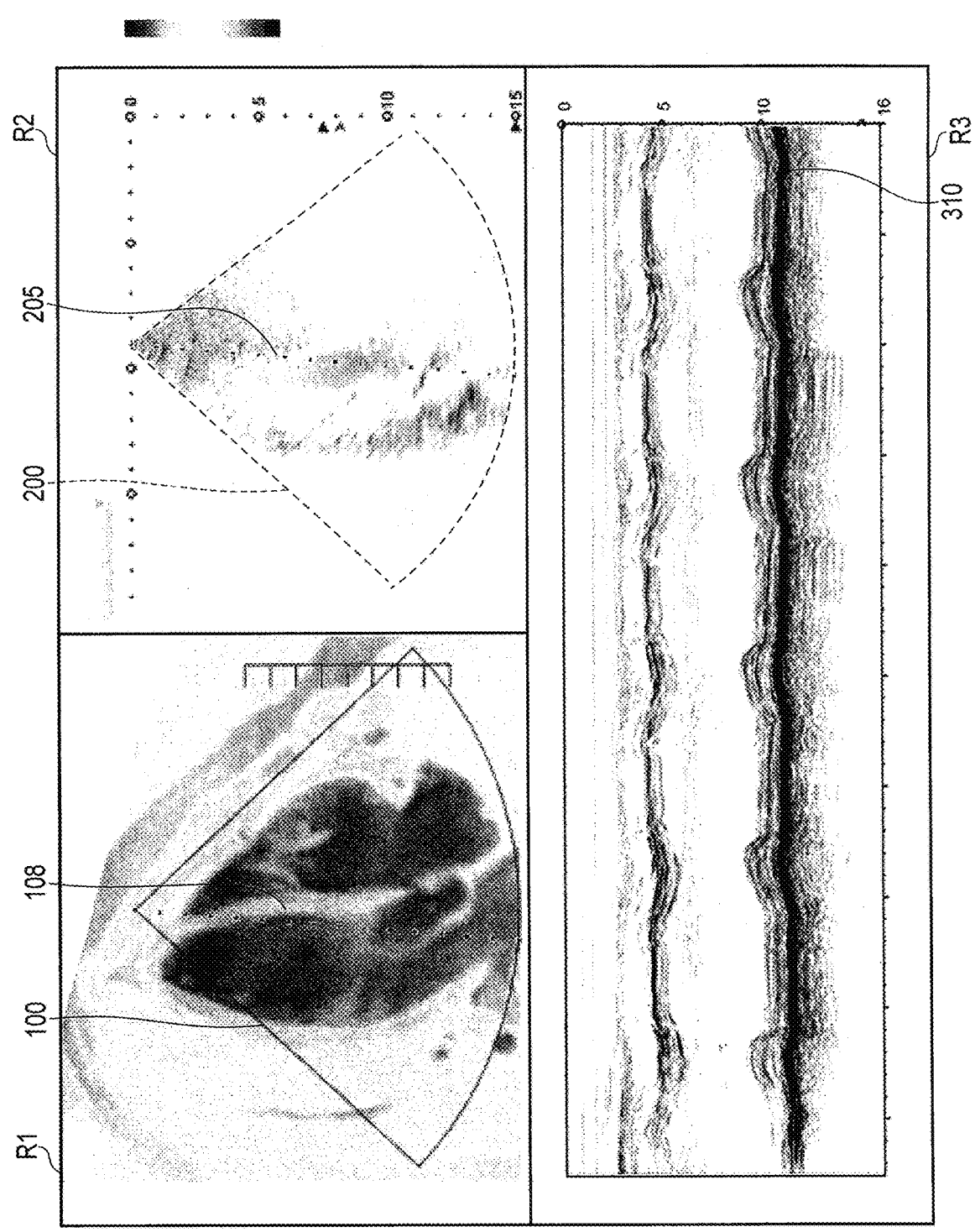
FIG. 12 is an example of a fusion image displayed on a display according to another embodiment.

FIG. 12 is an example of a fusion image (display image) displayed on a display according to another embodiment. The display image of FIG. 12 corresponds, for example, to an image while the M-mode scan is performed after the B-mode scan has been performed. The display image of FIG. 12 is divided into, for example, an image region R1, an image region R2 and an image region R3.

A B-mode image 200 is displayed in the image region R2. A cursor 205 is superimposed on the B-mode image 200. The cursor 205 indicates the direction to which ultrasonic waves are emitted in the M-mode.

An MPR image is displayed in the image region R1. A scanning range 100 and a cursor 108 are superimposed on the MPR image. The cursor 108 is similar to the cursor 205. The position of the cursor 108 is calculated based on the positional information of the ultrasonic probe 70 acquired during the M-mode scan.

An M-mode image 310 is displayed in the image region R3. The M-mode image 310 is acquired, for example, by the M-mode scan.

In sum, the display image of FIG. 12 includes a fusion image in which at least an MPR image and a B-mode image are simultaneously displayed, and a fusion image in which at least an MPR image and an M-image are simultaneously displayed. A cursor 108 is constantly displayed on the MPR image. Since the cursor 108 is constantly displayed on the MPR image, an operator can constantly recognize the acquisition position of the echo data.

Figure 13:
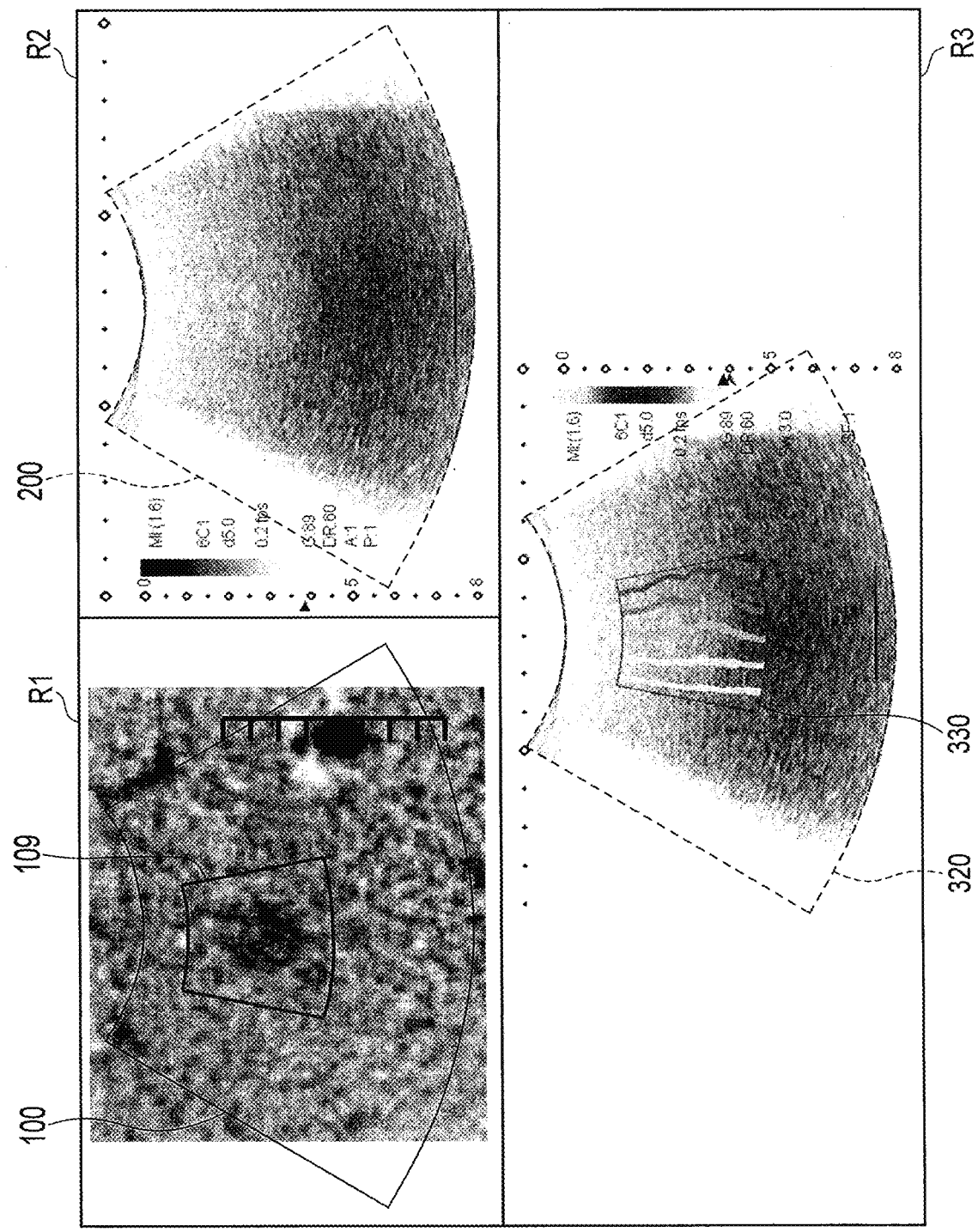
FIG. 13 is an example of a fusion image displayed on a display according to another embodiment.

FIG. 13 is an example of a fusion image (display image) displayed on a display according to another embodiment. The display image of FIG. 13 corresponds to an image obtained while the SWE mode scan is performed after the B-mode scan has been performed. The display image of FIG. 13 is divided into, for example, an image region R1, an image region R2 and an image region R3.

An MPR image is displayed in the image region R1. A scanning range 100 and an ROI marker 109 are superimposed on the MPR image. The ROI marker 109 indicates, for example, a range of a shear wave propagation speed display, an elasticity rate display, a propagation display, etc. in the SWE mode.

A B-mode image 200 is displayed in the image region R2. An ROI marker corresponding to the ROI marker 109 may be superimposed on the B-mode image 200.

An SWE image 320 is displayed in the image region R3. A propagation display image 330 is superimposed on the SWE image 320. The SWE image 320 is acquired, for example, by the SWE mode scan. The image superimposed on the SWE image 320 may be, for example, a shear wave propagation speed display image or an elasticity rate display image.

In sum, the display image of FIG. 13 includes a fusion image in which at least an MPR image and a B-mode image are simultaneously displayed, and includes a fusion image in which at least an MPR image and an SWE image are simultaneously displayed. The ROI marker 109 is constantly displayed on the MPR image. Since the ROI marker 109 is constantly displayed on the MPR image, an operator can constantly recognize the acquisition position of the echo data.

Figure 14:
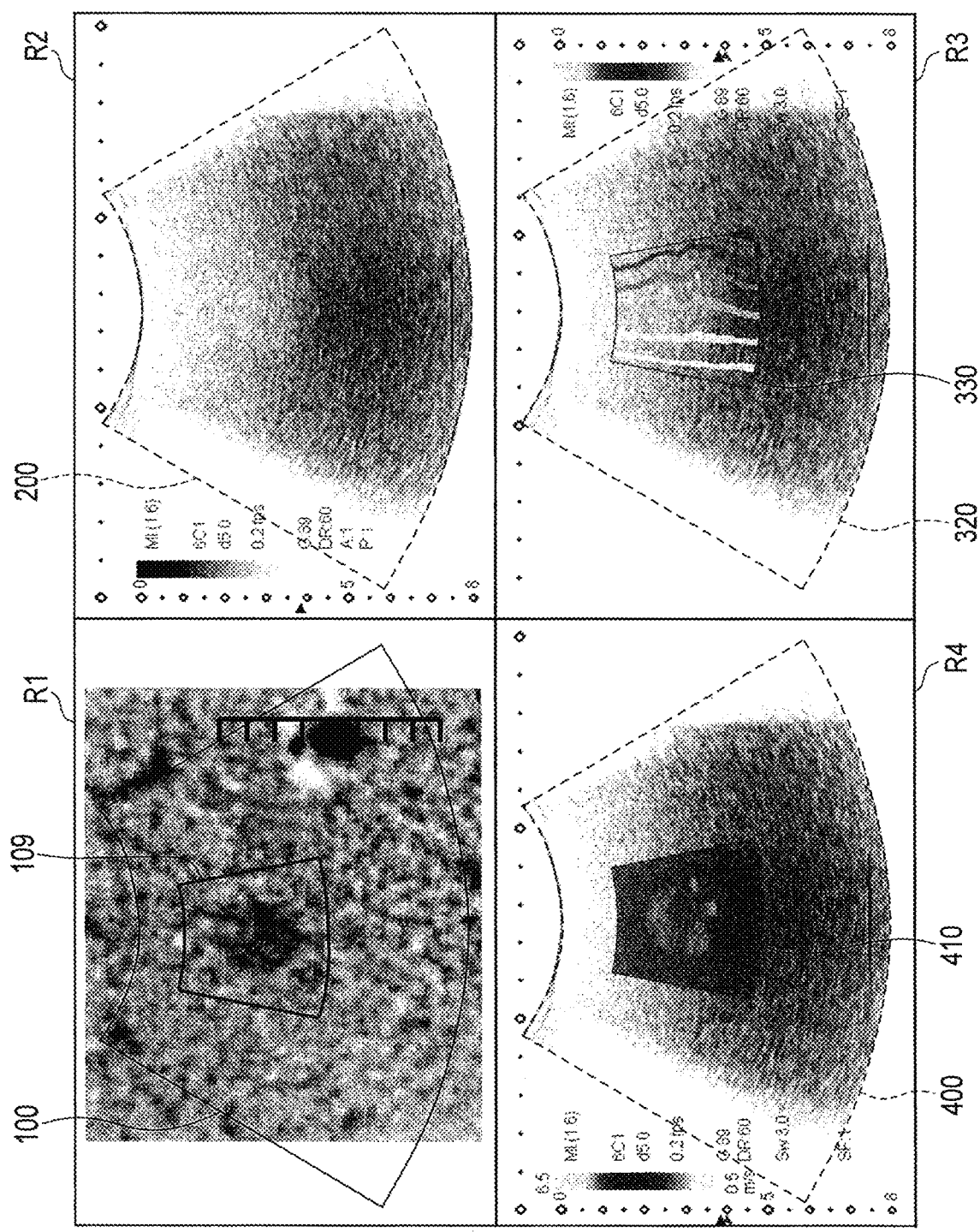
FIG. 14 is an example of a fusion image displayed on the display according to another embodiment.

FIG. 14 is an example of a fusion image (display image) displayed on a display according to another embodiment. The display image of FIG. 14 corresponds to an image while the SWE mode scan is performed after the B-mode scan has been performed. The display image of FIG. 14 is divided into, for example, an image region R1, an image region R2, and an image region R3 and an image region R4.

An MPR image is displayed in the image region R1. A scanning range 100 and an ROI marker 109 are superimposed on the MPR image. A B-mode image 200 is displayed in the image region R2. An SWE image 320 is displayed in the image region R3. A propagation display image 330 is superimposed on the SWE image 320.

An SWE image 400 is displayed in the image region R4. An elasticity rate display image 410 is superimposed on the SWE image 400. The SWE image 400 is acquired, for example, by the SWE mode scan. The image superimposed on the SWE image 400 may be a shear wave propagation speed display image.

In sum, the display image of FIG. 14 includes a fusion image in which at least an MPR image and a B-mode image are simultaneously displayed, and a fusion image in which at least an MPR image and an SWE image are simultaneously displayed. The ROI marker 109 is constantly displayed on the MPR image. Since the ROI marker 109 is constantly displayed on the MPR image, an operator can constantly recognize the acquisition position of the echo data.

According to at least one of the aforementioned embodiments, it is possible to assist recognition of the acquisition position of the echo data when the B-mode image is not acquired.

The term "processor" used in the above description refers to, for example, a CPU (Central Processing Unit), a GPU (Graphics Processing Unit), or circuitry such as an ASIC (Application Specific Integrated Circuit), a programmable logic device (for example, an SPLD (Simple Programmable Logic Device), a CPLD (Complex Programmable Logic Device), or an FPGA (Field Programmable Gate Array)). A processor implements functions by reading and executing a program stored in the storage circuitry. Each processor of the present embodiments is not limited to be configured as single circuitry, but may include a plurality of units of independent circuitry, in order to implement the functions. Furthermore, a plurality of constituent elements shown in FIGS. 1, and 5 may be integrated into one processor to implement the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
    processing circuitry configured to:
        receive a switching instruction to switch imaging modes from a first imaging mode to a second imaging mode;
        when in the first imaging mode,
            acquire first echo data by an ultrasonic probe executing an ultrasonic scan of a first scanning type,
            generate a first image including a B-mode image based on the first echo data,
            generate a cross sectional image corresponding to the B-mode image from pre-acquired volume data based on positional information acquired by a position sensor provided in the ultrasonic probe,
            direct a display to display the first image and the cross sectional image corresponding to the B-mode image; and
        when in the second imaging mode,
            acquire second echo data by the ultrasonic probe executing an ultrasonic scan of a second scanning type,
            generate a second image not including a B-mode image based on the second echo data,
            generate a cross sectional image corresponding to the second image from pre-acquired volume data based on positional information acquired by the position sensor; and
            direct a display to display the second image and the cross sectional image corresponding to the second image.

2. The ultrasonic diagnostic apparatus according to claim 1, wherein:
    the first image is a B-mode image, or a combined image of a B-mode image and a color Doppler image; and
    the second image is a Doppler spectrum image, an M-mode image, or an SWE image.

3. The ultrasonic diagnostic apparatus according to claim 1, wherein the second scanning type is a continuous wave (CW) type scan in which while continuous waves are transmitted, reflected waves are received.

4. The ultrasonic diagnostic apparatus according to claim 1, wherein the second scanning type is a pulse wave (PW) type scan in which pulse waves are transmitted to a plurality of scanning lines, and reflected waves are received.

5. The ultrasonic diagnostic apparatus according to claim 2, further comprising:
    a memory configured to store the cross sectional image corresponding to the second image generated in the second imaging mode,
    wherein the processing circuitry is further configured to:
    in response to an operation of designating a time phase on the Doppler spectrum image, a biological waveform, or the M-mode image, read from the memory the cross sectional image corresponding to the second image and corresponding to the designated time phase.

6. The ultrasonic diagnostic apparatus according to claim 1, wherein:
    the processing circuitry is further configured to:
        detect a positional shift of the ultrasonic probe based on positional information at the time when switching the imaging modes and positional information after switching the imaging modes, acquired by a position sensor provided in the ultrasonic probe; and
        notify the detected positional shift.

7. The ultrasonic diagnostic apparatus according to claim 1, wherein:
    the cross sectional image is either an X-ray image, an MRI image, an ultrasonic image, or a nuclear medicine image.

8. The ultrasonic diagnostic apparatus according to claim 1, wherein:
    the processing circuitry is further configured to:
        switch volume data based on which the cross sectional image is generated, synchronized with a biological waveform.

9. The ultrasonic diagnostic apparatus according to claim 1, wherein
    the processing circuitry is further configured to:
        direct the display to display the cross sectional image on which information related to an ultrasonic image in accordance with various types of imaging modes is superimposed.

10. An ultrasonic diagnostic apparatus comprising:
    processing circuitry configured to:
        receive a switching instruction to switch imaging modes from a first imaging mode to a second imaging mode;
        when in the first imaging mode,
            acquire first echo data by an ultrasonic probe executing an ultrasonic scan of a first scanning type
            generate a first image including a B-mode image based on the first echo data
        when in the second imaging mode, acquire second echo data by the ultrasonic probe executing an ultrasonic scan of a second scanning type,
generate a second image not including a B-mode image based on the second echo data,
detect a positional shift of the ultrasonic probe based on positional information at the time when switching the imaging modes and positional information after switching the imaging modes, acquired by a position sensor provided in the ultrasonic probe; and
notify the detected positional shift.

11. The ultrasonic diagnostic apparatus according to claim 10, wherein the processing circuitry is further configured to direct a display to display at least the first image in the first imaging mode, and to display at least the second image in the second imaging mode.

12. The ultrasonic diagnostic apparatus according to claim 10, wherein:
the first image is a B-mode image, or a combined image of a B-mode image and a color Doppler image; and
the second image is a Doppler spectrum image, an M-mode image, or an SWE image.

13. A non-transitory computer readable medium storing a computer program which is executed by a computer to provide the steps of:
receiving a switching instruction to switch imaging modes from a first imaging mode to a second imaging mode;
when in the first imaging mode,
acquiring first echo data by an ultrasonic probe executing an ultrasonic scan of a first scanning type,
generating a first image including a B-mode image based on the first echo data,
generating a cross sectional image corresponding to the B-mode image from pre-acquired volume data based on positional information acquired by a position sensor provided in the ultrasonic probe; and
directing a display to display the first image and the cross sectional image corresponding to the B-mode image; and
when in the second imaging mode,
acquiring second echo data by the ultrasonic probe executing an ultrasonic scan of a second scanning type,
generating a second image not including a B-mode image based on the second echo data,
generating a cross sectional image corresponding to the second image from pre-acquired volume data based on positional information acquired by the position sensor; and
directing a display to display the second image and the cross sectional image corresponding to the second image.

14. The non-transitory computer readable medium as claimed in claim 13, wherein:
the first image is a B-mode image, or a combined image of a B-mode image and a color Doppler image; and
the second image is a Doppler spectrum image, an M-mode image, or an SWE image.

15. The non-transitory computer readable medium as claimed in claim 13, wherein the second scanning type is a continuous wave (CW) type scan in which while continuous waves are transmitted, reflected waves are received.

16. The non-transitory computer readable medium as claimed in claim 13, wherein the second scanning type is a pulse wave (PW) type scan in which pulse waves are transmitted to a plurality of scanning lines, and reflected waves are received.

17. A non-transitory computer readable medium storing a computer program which is executed by a computer to provide the steps of:
receiving a switching instruction to switch imaging modes from a first imaging mode to a second imaging mode;
when in the first imaging mode,
acquiring first echo data by an ultrasonic probe executing an ultrasonic scan of a first scanning type,
generating a first image including a B-mode image based on the first echo data,
when in the second imaging mode,
acquiring second echo data by the ultrasonic probe executing an ultrasonic scan of a second scanning type,
generating a second image not including a B-mode image based on the second echo data,
detecting a positional shift of the ultrasonic probe based on positional information at the time when switching the imaging modes and positional information after switching the imaging modes, acquired by a position sensor provided in the ultrasonic probe; and
notifying the detected positional shift.

* * * * *